US011273104B2

(12) United States Patent
Furuhashi et al.

(10) Patent No.: US 11,273,104 B2
(45) Date of Patent: *Mar. 15, 2022

(54) PHOTOCURABLE COMPOSITION AND DENTAL RESTORATION FILLING MATERIAL

(71) Applicant: TOKUYAMA DENTAL CORPORATION, Tokyo (JP)

(72) Inventors: Koji Furuhashi, Tokyo (JP); Hironobu Akizumi, Tokyo (JP)

(73) Assignee: TOKUYAMA DENTAL CORPORATION, Tokyo (JP)

(*) Notice: Subject to any disclaimer, the term of this patent is extended or adjusted under 35 U.S.C. 154(b) by 5 days.

This patent is subject to a terminal disclaimer.

(21) Appl. No.: 16/491,143

(22) PCT Filed: Mar. 5, 2018

(86) PCT No.: PCT/JP2018/008396
§ 371 (c)(1),
(2) Date: Sep. 4, 2019

(87) PCT Pub. No.: WO2018/164074
PCT Pub. Date: Sep. 13, 2018

(65) Prior Publication Data
US 2020/0069534 A1 Mar. 5, 2020

(30) Foreign Application Priority Data
Mar. 6, 2017 (JP) .............................. JP2017-042091

(51) Int. Cl.
A61K 6/62 (2020.01)
A61K 6/887 (2020.01)
A61K 6/853 (2020.01)
A61K 6/878 (2020.01)
A61K 6/84 (2020.01)
A61K 6/17 (2020.01)

(52) U.S. Cl.
CPC ................. A61K 6/62 (2020.01); A61K 6/17 (2020.01); A61K 6/84 (2020.01); A61K 6/853 (2020.01); A61K 6/878 (2020.01); A61K 6/887 (2020.01)

(58) Field of Classification Search
CPC .......... A61K 6/62; A61K 6/887; A61K 6/853; A61K 6/878; A61K 6/84; A61K 6/17; A61K 6/16; A61K 6/54; A61K 6/76
See application file for complete search history.

(56) References Cited

U.S. PATENT DOCUMENTS

| 3,729,313 | A | 4/1973 | Smith |
| 3,741,769 | A | 6/1973 | Smith |
| 4,020,557 | A | 5/1977 | Rockett et al. |
| 5,545,676 | A | 8/1996 | Palazzotto et al. |
| 8,993,650 | B2 | 3/2015 | Uchida et al. |
| 2004/0180983 | A1 | 9/2004 | Hara et al. |
| 2008/0319104 | A1 | 12/2008 | Klapdohr et al. |
| 2010/0081728 | A1 | 4/2010 | Uchida et al. |
| 2011/0196062 | A1 | 8/2011 | Craig |
| 2013/0096226 | A1 | 4/2013 | Toriyabe et al. |
| 2013/0172441 | A1 | 7/2013 | Takahata et al. |
| 2014/0206792 | A1 | 7/2014 | Ishizaka et al. |
| 2014/0213687 | A1 | 7/2014 | Yamazaki et al. |
| 2014/0295376 | A1 | 10/2014 | Uchida et al. |
| 2015/0094396 | A1 | 4/2015 | Nakatsuka et al. |
| 2015/0272833 | A1 | 10/2015 | Toriyabe et al. |
| 2016/0008232 | A1 | 1/2016 | Toriyabe et al. |
| 2017/0049665 | A1 | 2/2017 | Kita et al. |
| 2017/0196667 | A1 | 7/2017 | Teramae et al. |
| 2018/0303721 | A1 | 10/2018 | Akizumi et al. |
| 2019/0192386 | A1 | 6/2019 | Fukudome et al. |

FOREIGN PATENT DOCUMENTS

| CN | 102905673 A | 1/2013 |
| EP | 1236459 A1 | 9/2002 |
| EP | 2583660 A1 | 4/2013 |
| EP | 2902007 A1 | 8/2015 |
| EP | 3366269 A1 | 8/2018 |
| EP | 3536302 A1 | 9/2019 |
| JP | S60011505 A | 1/1985 |

(Continued)

OTHER PUBLICATIONS

H. Shinoda et al., "Shikisai Kogaku Nyumon", Morikita Publishing Co., Ltd., 1st print published on May 1, 2007, pp. 73-78, Partial English translation attached (10 pages).

K. Saito et al., "Hikari to Shikisai no Kagaku", Kodansha, Ltd., 1st print published on Oct. 20, 2010, pp. 118-139, Partial English translation attached (21 pages).

The Color Science Association of Japan, ed., "Handbook of Color Science (3rd Edition)", University of Tokyo Press, published in Apr. 2011, pp. 1130-1181, Partial English translation attached (35 pages).

JIS Z 8102 (CSAJ/JSA), Names of non-luminous object colours, 2001, Partial English translation attached (16 pages) JIS Z 8110, Colour specification—Names of light-source colour, 1995, Partial English translation attached (9 pages).

(Continued)

Primary Examiner — Jessica M Roswell
(74) Attorney, Agent, or Firm — Osha Bergman Watanabe & Burton LLP

(57) ABSTRACT

Provided is a photocurable composition that contains a polymerizable monomer (A), a spherical filler (B) having an average particle size within the range of 230-1000 nm, and a polymerization initiator (C), the photocurable composition being such that: 90% or more of the individual particles that constitute the spherical filler (B) are within a range of ±5% of the average particle size; the polymerizable monomer (A) and the spherical filler (B) satisfy condition (X1) represented by formula (1): nP<nF (where nP represents the refractive index at 25° C. of a polymer obtained by polymerizing the polymerizable monomer (A), and nF represents the refractive index at 25° C. of the spherical filler (B)); and the polymerization initiator (C) includes a photosensitizing compound (C1), a tertiary amine compound (C2), and a photoacid generator (C3).

8 Claims, No Drawings

(56) References Cited

FOREIGN PATENT DOCUMENTS

| | | |
|---|---|---|
| JP | S62-086003 A | 4/1987 |
| JP | S63-218703 A | 9/1988 |
| JP | S63-273602 A | 11/1988 |
| JP | 2001-239661 A | 9/2001 |
| JP | 2004-276492 A | 10/2004 |
| JP | 2005-089729 A | 4/2005 |
| JP | 2006117543 A | 5/2006 |
| JP | 2007-532518 A | 11/2007 |
| JP | 201083833 A | 4/2010 |
| JP | 2010215694 A | 9/2010 |
| JP | 2012-505823 A | 3/2012 |
| JP | 2012-087086 A | 5/2012 |
| JP | 2012-153640 A | 8/2012 |
| JP | 2014-189503 A | 10/2014 |
| JP | 2015-067594 A | 4/2015 |
| JP | 2016-169180 A | 9/2016 |
| RU | 2472708 C2 | 1/2013 |
| WO | 2009/014031 A1 | 1/2009 |
| WO | 2010045105 A1 | 4/2010 |
| WO | 2011/158742 A1 | 12/2011 |
| WO | 2012/042911 A1 | 4/2012 |
| WO | 2012/176877 A1 | 12/2012 |
| WO | 2013/039169 A1 | 3/2013 |
| WO | 2014/050634 A1 | 4/2014 |
| WO | 2014148293 A1 | 9/2014 |
| WO | 2015/125470 A1 | 8/2015 |
| WO | 2015141683 A1 | 9/2015 |
| WO | 2017/069274 A1 | 4/2017 |
| WO | 2018/043595 A1 | 3/2018 |
| WO | 2018/101236 A1 | 6/2018 |

OTHER PUBLICATIONS

H. Matsumura et al., rev.,"Adhesion Yearbook 2006", 1st Edition, Quintessence Publishing Co., Ltd., published in Aug. 2006, pp. 129-137, Partial English translation attached (14 pages).
M. Miyazaki, "Science & Technique of Composite Resin Restoration", 1st Edition, Quintessence Publishing Co., Ltd., published in Jan. 2010, pp. 48-49, Partial English translation attached (6 pages).
H. Hosoda, ed., "Basics of Photopolymerizable Composite Resins and Clinics", Nippon Shika Shuppan Co., Feb. 10, 1986, pp. 9-20, Partial English translation attached (9 pages).
T. Yamaoka, ed., "Dictionary of Applied Optical Technologies and Materials", published by Industrial Technical Service Center Co., Ltd., Apr. 26, 2006, pp. 108-112, Partial English translation attached (4 pages).
Chemical Society of Japan, ed., "Chemistry Handbook, Fundamentals-II, Third Revision", published by Maruzen, Inc., Jun. 25, 1984, pp. 337-345 (5 pages).
International Search Report issued in International Application No. PCT/JP2018/008396, dated Apr. 17, 2018 (2 pages).
Written Opinion issued in International Application No. PCT/JP2018/008396, dated Apr. 17, 2018 (4 pages).
Office Action issued in corresponding Brazilian Application No. BR1120190094563, dated Jul. 1, 2020 (47 pages).
Extended European Search Report issued in the European Application No. 17876044.3, dated Oct. 25, 2019 (13 pages).
International Search Report including Written Opinion issued in the International Application No. PCT/JP2017/042522 dated Jan. 23, 2018 (14 pages).
J. Yamagawa, "New Standard of Hybrid Arising from Pursuit of Lasting Aesthetics—Hybrid-type Hardness Region (pearl aesthetics)", Japanese Dental Technologists Association, 2011, No. 503, pp. 5-8 (6 pages).
International Search Report including Written Opinion issued in the International Application No. PCT/JP2018/015734, dated Jun. 12, 2018 (15 pages).
Office Action issued in the U.S. Appl. No. 16/605,602, dated Jun. 5, 2020 (10 pages).
International Search Report including Written Opinion issued in the International Application No. PCT/JP2018/015735 dated Jul. 24, 2018 (19 pages).
Office Action issued in the U.S. Appl. No. 16/605,617, dated Jul. 10, 2020 (12 pages).
Office Action issued in the U.S. Appl. No. 16/465,018, dated Jul. 10, 2020 (10 pages).
Office Action issued in the related Russian Patent Application No. RU2019134976, dated Mar. 23, 2021 (11 pages).
Extended European Search Report issued in the corresponding European Application No. 18763621.2, dated Oct. 22, 2020 (10 pages).
Extended European Search Report issued in the related European Application No. 18788652.8, dated Oct. 23, 2020 (8 pages).
Final Office Action issued in the related U.S. Appl. No. 16/605,602, dated Dec. 8, 2020(13 pages).
Pre-grant Opposition filed by Dentscare LTDA on Apr. 6, 2020 for BR Application No. BR112018006772-5 (39 pages).
Office Action issued in the Russian Application No. 2018116597, dated Nov. 26, 2019 (15 pages).
Office Action issued in the Chinese Application No. 201680061397.2, dated Nov. 16, 2018 (13 pages).
Office Action issued to Korean Application No. 10-2018-7007737, dated Jul. 5, 2018 (7 pages).
International Search Report issued in International Application No. PCT/JP2016/081367 dated Dec. 27, 2016 (5 pages).
International Preliminary Report on Patentability issued in International Application No. PCT/JP2016/081367 dated Jun. 20, 2017 (11 pages).
Extended European Search Report issued in European Application No. 18787662.8, dated Dec. 17, 2020 (6 pages).

PHOTOCURABLE COMPOSITION AND DENTAL RESTORATION FILLING MATERIAL

TECHNICAL FIELD

The present invention relates to a photocurable composition, and particularly, to a photocurable composition that is useful for applications such as dental materials, inks, films, and construction materials, and above all, useful as a dental material. More particularly, the invention relates to a photocurable composition that can have the external appearance color tone well-controlled without using a dye or a pigment, exhibits reduced decoloration and discoloration, and contains a polymerization initiator which is stable to ambient light (light of weak intensity) compared to conventional polymerization initiators, but rapidly allows complete polymerization in a remarkably short time by irradiation with strong light using an irradiator such as a halogen lamp, a xenon lamp, or a laser diode so that superior physical properties of a cured product are obtained, and particularly, to a photocurable composition useful as a dental filling restorative material that provides excellent convenience and esthetics.

BACKGROUND ART

In a variety of fields such as dental materials, recording materials, and construction materials, curable compositions including polymerizable monomers and inorganic or organic fillers have been conventionally used. Particularly in the field of dental filling restorative materials, since curable compositions can impart a color tone equivalent to the natural teeth color and is easily operable, curable compositions have been rapidly popularized as materials for restoring teeth that have been damaged by dental caries, fracture, and the like. In recent years, as a result of an enhancement of the mechanical strength and an enhancement of the adhesive force to teeth, curable compositions are also used for the restoration of anterior teeth as well as for molar teeth to which high occlusal pressure is exerted. For example, Patent Document 1 discloses a composite composition for photopolymerization having excellent depth of cure, the composition including a polymerizable vinyl monomer; an inorganic oxide having a refractive index that is lower than the refractive index of a polymer of the vinyl monomer and including particles having' a particle size of 0.1 µm to 1.0 µm; and a catalyst capable of initiating photopolymerization by visible light. Furthermore, Patent Document 2 discloses a composite composition for photopolymerization having excellent depth of cure, from which a compound having an adequate degree of translucency is obtained, the composition including a polymerizable vinyl monomer; a filler having a refractive index that is higher than the refractive index of a polymer of the vinyl monomer; a filler having a refractive index that is lower than the refractive index of the relevant polymer; and a catalyst capable of initiating photopolymerization by visible light.

For the color tone adjustment of conventional curable compositions such as the compositions of Patent Documents 1 and 2, pigments, dyes, and the like have been used, and various color tones have been prepared by varying the mixing ratios of pigments, dyes, and the like, which have different color tones. However, coloration by means of pigments and dyes tends to undergo decoloration or discoloration caused by aged deterioration. In regard to dental filling restorative materials, a curable composition including pigments, dyes, and the like exhibits high color tone adaptability immediately after restoration; however, after restoration, the curable composition is discolored as time elapses, and a phenomenon that the external appearance of the restored site becomes incompatible with the appearance of natural teeth, occurs in many cases.

In this regard, as a structure that can be colored without using a pigment, a dye, or the like, it has been known to utilize structural color that is expressed by interference, diffraction, refraction, scattering or the like of light. Generally, color (expression of color) of a material is such that when light having a certain wavelength is absorbed, light of other wavelengths is reflected or transmitted, and when the reflected light has a wavelength in the visible tight range, this light is perceived as color. This coloring (hue) is generally color developed by a natural or artificial dye or pigment, and is coloring resulting from energy exchange between light and an object. On the other hand, there is color that is not based on a dye or a pigment but is expressed only by means of the physical nature of light, without exchange of light energy. This is the structural color. A synonym for this is "interference color"; however, the interference color is a kind of structural color. The structural color is expressed by interference, diffraction, refraction, scattering, or the like of light. For example, the structural color is expressed in thin film interference caused by coating of spectacles or the like, multilayer film interference caused by a multilayer configuration of thin films, diffraction grating, and a photonic crystal. These have regular structures having constant intervals; however, these are not ordered structures. For example, the structural color is expressed also by scattering caused by fine particles dispersed in a matrix (thus, regarding the structural color, see Non-Patent Documents 1 to 4). For example, Patent Document 3 discloses a recorded matter exhibiting coloration of light by means of interfered light, the recorded matter having sites where solid fine particles aggregate and arrange on a liquid-repellent surface of a material to be recorded and form a regular periodic structure, in which the liquid-repellent surface has black color or a dark color having a standard color chart value of 6 or less and having a chroma of 8 or less. Patent Document 4 discloses a color sheet that does not use a coloring dye or pigment and visually presents a chromatic color as a structural color, in which organic or inorganic spherical particles having black achromatic color and having an average particle size (d) in the range of 100 nm to 500 nm as represented on a volume basis, are regularly aligned on a color-developing base material sheet and form a particulate laminate thereon. Coloring by such a structural color that utilizes interference, diffraction, refraction, scattering or the like of light has an advantage that a phenomenon of decoloration or discoloration appearing in the case of using pigments, dyes or the like is not observed.

In recent years, in the field of dental filling restorative materials, there is an increasing demand not only for the recovery of occlusion but also for esthetic restoration of the appearance looking like natural teeth. There is a demand for a restorative material which can reproduce not only simple equivalent color tones but also the transparency or color tone at various restoration sites of teeth, and which undergoes aged deterioration to a reduced extent. From this point of view, in both of the compositions of Patent Documents 1 and 2, the particle size distribution of the filler or the relation between the refractive indices of the polymer as a matrix and the filler were not optimized, coloring by a structural color was not always obtained, and since the compositions were colored using a pigment or the like, a phenomenon of decoloration or discoloration caused by aged deterioration occurred.

Thus, Patent Document 5 discloses a curable dental material having high esthetic properties and exhibiting adjustable translucency and high opalescence, the curable dental material containing a monomer having a refractive index of lower than 1.45, an opalescent filler having a refractive index of lower than 1.45, another conventional filler or filler mixture, and at least one selected from the group consisting of a polymerization initiator, a stabilizer, and a colorant, in which the difference between the refractive index of the monomer and the refractive index of the opalescent filler is less than or equal to 0.04, and the average particle size of the opalescent filler is 230 nm±50 nm. However, in the material of Patent Document 5, since the relation between the refractive index of a polymer of the monomer and the refractive index of the opalescent filler is not optimized, coloring by a structural color is not necessarily sufficient, and the range of the average particle size is limited to a range that exhibits opalescence. Thus, it was difficult to reproduce the transparency and color tone at various restoration sites of teeth.

Patent Document 6 discloses a dental composite restorative material which exhibits an opal effect (the same unique light scattering phenomenon as that of mineral opal) and provides excellent esthetic properties, the dental composite restorative material including: W a polymerizable monomer; (B) spherical silica-based particles having an average particle size in the range of 0.1 μm to 0.5 μm and a standard deviation of the particle size distribution of 1.30 or less; (C) an organic-inorganic composite filler obtained by dispersing these silica-based particles in an organic resin matrix; and (D) a polymerization initiator, in which the difference between the refractive index of the spherical silica-based particles and the refractive index of a polymer obtained by polymerizing the polymerizable monomer is 0.1 or less, and the difference between the refractive index of the organic-inorganic composite filler and the refractive index of a polymer obtained by polymerizing the polymerizable monomer is 0.1 or less. However, in regard to Patent Document 6, the occasion of obtaining an opal effect is substantially limited to a case in which the refractive index of the polymer is larger than the refractive indices of the spherical silica-based particles and the organic-inorganic composite filler, and the opal effect exhibits a bluish color. A bluish-colored dental composite restorative material is suitable for the restoration of an incisal part of a tooth; however, this material is not necessarily suitable particularly for the restoration of the tooth cervix, where reproduction of the hue of the yellowish to reddish dentinal color is necessary. As such, in regard to the material of Patent Document 6, since the relation between the refractive indices of the polymer and the filler s not optimized, it is difficult to reproduce the color tones of various restoration sites of teeth.

As explained above, it is required for a composite restorative material to exactly reproduce the color tones of teeth at various treated sites. The crown part of a natural tooth formed from dentine and enamel, and the color tone (hue, chrome, and value) varies from site to site. For example, since an incisal part has a thin dentinal layer and is almost covered with enamel, the incisal part is highly transparent and exhibits a bluish hue. In contrast, the tooth cervix is opaque because the deep part has a thick dentinal layer, and compared to an incisal part, the tooth cervix has high value (lightness or darkness of color) and high chroma (vividness of color) and has the yellowish to reddish hue of the dentinal color. That is, the chroma and value decrease in the direction from the tooth cervix having a thick dentinal layer at the deep part, toward the incisal part having a thin dentinal layer. Furthermore, the incisal part, which is formed from almost enamel only, shows a bluish hue; however, the other parts show a yellowish to reddish hue in reflection of the hue of the dentinal layer at the deep part. As such, since a tooth has different color tones at different sites, in order to obtain superior esthetic properties for tooth restoration, it is important to prepare a plurality of curable pastes for restoration having different color tones, and to select and use, from among these curable pastes for restoration, a curable paste having a color tone that best matches the actual restored tooth and adjacent teeth thereof (hereinafter, also referred to as "periphery of the restored tooth") (Non-Patent Document 5).

Such selection of color tone is achieved by a dentist, who uses a shade guide (color sample) that includes a collection of various cured product samples of prepared curable pastes, compares the respective color tones of the samples with the color tone of the periphery of the restored tooth checked by looking into the oral cavity, and selecting a color tone that is felt to be closest to the color tone of the restored tooth.

Furthermore, as long as it is not the case that the damage of the restored tooth is small with a shallow cavity, it is difficult to realize the adaptation of the color tone by means of filling of a single kind of curable paste. That is, if the cavity is deep (for example, Class 4 cavity), the color tone of a tooth is visually perceived in a state in which not only the color tone of the tooth flank part (enamel portion) but also the color tone of the deep part (dentinal portion) that shows through are combined to give a rich gradation. Therefore, by filling a deep cavity by laminating the curable pastes to be filled while varying the color tone at a certain interval of depth, this subtle color one is reproduced. Usually, this reproduction of color tone is carried out such that a plurality of curable pastes for dentinal restoration, which reproduce the color tones of the dentinal portion, are used and laminated from the deepest part (usually, lamination is continued while each layer 5 cured), and a curable paste for enamel restoration is laminated at the last surface layer (for example, see Non-Patent Documents 5 and 6).

As such, since there are individual differences and site differences in the color tone of teeth, arranging curable pastes having their color tones strictly controlled in consideration of these differences, is substantially impossible because a huge number of curable pastes are needed. Particularly, in the restoration of a cavity in which the dentine is positioned at the surface of deep parts, since the color has high value and high chroma and has a yellowish to reddish hue (in many cases, reddish hue of red-yellow to red-brown), and there is a large variation depending on individual differences and site differences, strict control of the color tone as described above is even more difficult.

Furthermore, restoration of a tooth is achieved by curing a filled curable paste by photopolymerization, from the viewpoint that there is no need of a mixing operation and the curing operation is convenient (see, for example, Non-Patent Document 6). That is, a photocurable paste is obtained by adding a polymerization initiator that generates a radical or an ion species by light irradiation, to a paste-like composition containing a polymerizable monomer and a filler as main components, and the photocurable paste is used by filling a cavity with the photocurable paste and then irradiating the photocurable paste with light to cure using a light irradiator for exclusive use. In the following description, the light that is radiated in order to achieve polymerization and curing may be referred to as "active light". Generally, such active light is radiated using a light source with an output power of a light intensity of about 100 mW/cm$^2$ to 1,500 mW cm$^2$ in a wavelength region of about 360 nm to 500 nm (this is a principal absorption region of an α-diketone compound known as a polymerization initiator), from a distance of about 0 mm to 10 mm. For example, restoration of a tooth is achieved by, in a dental clinic, filling a cavity of a tooth to be restored with a photocurable paste, shaping the photocurable paste into the form of the tooth, subsequently irradiating the photocurable paste with active light using a light irradiator for exclusive use, and thereby polymerizing and curing the photocurable paste. Furthermore, restoration of a tooth is also achieved by, in a dental technical factory, building up a photocurable paste on a plaster cast into the form of a tooth to be restored, polymerizing and curing this photocurable paste by light irradiation, and then, in a dental clinic, adhering the obtained cured body to the dentine using a dental adhesive (see, for example, Non-Patent Document 7).

With regard to the photopolymerization initiator, various suggestions have been made, and generally, a compound that is decomposed per se by absorbing light and thereby produces a polymerization active species, and a system obtained by combining such a compound with an appropriate sensitizer have been widely investigated and used.

As an example of the former, acylphosphine oxide compounds and α-diketone compounds are known, and in particular, α-diketone compounds exhibit polymerization initiation ability in the wavelength region of visible light, which has little influence on the human body (for example, camphor-quinone, which is a representative α-diketone compound, is a yellow compound having a maximum absorption wavelength at 468 nm). Furthermore, as an example of the latter, a combination of an α-diketone compound and a tertiary amine compound is well known, and such a combination is usefully used in the field of dental materials because α-diketone compounds exhibit a polymerization initiation ability in the wavelength region of visible light.

However, in a case in which a combination of an α-diketone compound and a tertiary amine compound is used as a photopolymerization initiator, there is a problem that the viscosity of the paste increases while operations such as filling and building-up are carried out, and it becomes difficult to carry out the operations.

That is, operations such as filling and building-up of a paste need to be carried out under dental light that illuminates the oral cavity or white light such as an indoor light such as a fluorescent lamp (such light is referred to as ambient light), in order for an operator to visually recognize the shape of the paste and the color tone of a cured product obtainable by polymerization of the paste. General ambient light is adjusted to about 500 lux to 10,000 lux in consideration of visibility and the like. The light intensity may vary depending on the light source; however, the light intensity of the ambient light at 360 nm to 500 nm, which is a main absorption region of α-diketone compounds, is 1 mW/cm$^2$ or less, and this value is even lower than a few percent of the active light. However, a photopolymerization initiator comprising a combination of an α-diketone compound and a tertiary amine compound has satisfactory polymerization activity for light in the visible region, and because the photopolymerization initiator has superior polymerization activity, the photopolymerization initiator sensitively responds to ambient light such as described above and initiates curing. Therefore, when a process is carried out under ambient light that is inevitable in operations such as filling and building up, this high polymerization activity acts rather disadvantageously, curing proceeds slowly, and problems such as described above occur.

The phenomenon that the viscosity of a paste increases while operations such as filling and building up are carried out, can be avoided when the amount of addition of the photopolymerization initiator used is decreased, or the polymerization inhibitor is added sufficiently. However, in a case in which such a method is applied, sufficient curing does not occur even when active light is radiated for a time period to the same extent as conventional cases, and problems such as the strength of the cured product thus obtainable being decreased, and unpolymerized monomer remaining in a large quantity near the surface of the cured product, frequently occur. Therefore, in order to sufficiently carry out polymerization and curing, it is necessary to prolong the time for radiating active light. However, photocurable pastes are used in the oral cavity of a patient in many cases, and there is a problem with prolongation of the irradiation time in that not only the operation takes time, but also a heavy burden is placed on the patient. Thus, it is the current situation that shortening of the irradiation time (curing time) is desired.

Furthermore, even for a photocurable paste having the stability to ambient light increased by reducing the amount of addition of the photopolymerization initiator, shortening of the curing time or increasing of the cured product strength can be attempted by increasing the light intensity of the active light to be radiated; however, in order to increase the light intensity, a large quantity of energy is needed to that extent. Furthermore, even for visible light, there is a possibility that excessively strong light may cause damage to the human body, particularly to the eyes. Moreover, since a light source with high light intensity generally tends to exhibit strong heat generation, there is a risk that excessively strongly light may also cause damage to the living body due to the heat. That is, in a method of decreasing the amount of addition of the photopolymerization initiator, in a case in which a light irradiator such as a laser diode that is generally used is used, shortening of the curing time or increasing of the strength of the cured product cannot be attempted, and it is difficult to carry out polymerization and curing rapidly and sufficiently without imposing any burden on the patient.

As such, with a photocurable paste having a conventional polymerization initiator incorporated therein, the stability to ambient light could not be increased without impairing the reaction activity to active light. That is, a photocurable paste having a characteristic that curing does not occur under light of weak intensity, such as ambient light, and curing occur rapidly when the paste is irradiated with active light using a light irradiator that is generally used for use in dentistry, cannot be obtained.

In order to solve such a problem, various photopolymerization initiators other than a combination of an α-diketone compound and a tertiary amine compound have been investigated. For example, investigation is being conducted on a system in which a photoacid generator has been added to a photosensitizing compound and a tertiary amine compound, and as an example thereof, a photopolymerization initiator including an aryliodonium salt, a compound for sensitization, and an electron-donating compound is known (see, for example, Patent Document 7).

For a photocurable paste containing such a polymerization initiator component, the active light irradiation time required for polymerization and curing is made shorter compared to conventional cases. However, aryliodonium salts that are suitably used are described in Patent Documents 7, 8, and 9; however, the details on how the type of the aryliodonium salt may affect the polymerization activity are not known.

Furthermore, as another example of the system obtained by adding a photoacid generator to a photosensitizing compound and a tertiary amine compound, a photopolymerization initiator including an α-diketone compound, an aromatic amine compound, an aliphatic amine compound, and an s-triazine compound having a trihalomethyl group as a substituent, is known (see, for example, Patent Document 10).

Patent Document 1: Japanese Unexamined Patent Application, Publication. No. S62-86003

Patent Document 2: Japanese Unexamined Patent Application, Publication No. S63-218703

Patent Document 3: Japanese Unexamined Patent Application, Publication No. 2001-239661

Patent Document 4: Japanese Unexamined Patent Application, Publication No. 2004-276492

Patent Document 5: Japanese Unexamined Patent Application (Translation of PCT Application), Publication No. 2007-532518

Patent Document 6: PUT International Publication No. WO2011/158742

Patent Document 7: Japanese Unexamined Patent Application, Publication No. S63-273602

Patent Document 8: U.S. Pat. No. 3,729,313, Specification

Patent Document 9: U.S. Pat. No. 3,741,769, Specification

Patent Document 10: Japanese Unexamined Patent Application, Publication No. 2005-89729

Non-Patent Document 1: SHINODA, Hiroyuki and FUJIEDA, Ichiro, "Shikisai Kogaku Nyumon", Morikita Publishing Co., Ltd., $1^{st}$ print published on May 1, 2007, pp. 73-78

Non-Patent Document 2: SAITO, Katsuhiro, et al., "Hikari to Shikisai no Kagaku", Kodansha, Ltd., $1^{st}$ print published on Oct. 20, 2010, pp. 118-139

Non-Patent Document 3: The Color Science Association of Japan, ed., "Handbook of Color Science ($3^{rd}$ Edition)", University of Tokyo Press, published in April, 2011, pp. 1130-1181

Non-Patent Document 4: JIS Z8102, Z8110

Non-Patent Document 5: MATSUMURA, Hideo and TAGAMI, Junji, rev., "Adhesion Yearbook 2006", $1^{st}$ Edition, Quintessence Publishing Co., Ltd., published in August, 2006, pp. 129-137

Non-Patent Document 6: MIYAZAKI, Masashi, "Science & Technique of Composite Resin Restoration", $1^{st}$ Edition, Quintessence Publishing Co., Ltd., published in January, 2010, pp. 48-49

Non-Patent Document 7: HOSODA, Hiroyasu, ed., "Basics of Photopolymerizable Composite Resins and Clinics", Nippon Shika Shuppan. Co., Feb. 10, 1986, p. 9-20

Non-Patent Document 8: YAMAOKA, Tsuguo, ed., "Dictionary of Applied Optical Technologies and Materials", published by Industrial Technical Service Center Co., Ltd., Apr. 26, 2006, p. 108-112

Non-Patent Document 9: Chemical Society of Japan, ed., "Chemistry Handbook, Fundamentals-II, Third Revision", published by Maruzen, Inc., Jun. 25, 1984, p. 337-345

DISCLOSURE OF THE INVENTION

Problems to be Solved by the Invention

Restoration of teeth using a curable composition that utilizes light colored by a structural color caused interference, diffraction, refraction, scattering or the like of light, is advantageous because a colorant substance such as a pigment may not be used. However, for the restoration of teeth, a curable composition that can be adapted by using the smallest possible number of color species, to the color tone of natural teeth that exhibits individual differences or shades of color depending on the restoration site, is desirable. Furthermore, in a case in which the curable composition is cured by photopolymerization, there is an advantage that a mixing operation is not needed, and the process is convenient. However, it is desirable that the photocurable composition does not undergo curing over a sufficient time at the time of operation such as building up, or the like of the photocurable composition, while polymerization and curing is completed rapidly upon irradiation with active light.

Therefore, an object of the present invention is to provide a photocurable composition having satisfactory restoration workability for a cavity, particularly a cavity including dentine in the deep part, the photocurable composition forming a cured product having an appearance that matches the appearance of natural teeth and sustains the match with natural teeth for a long time period, the photocurable composition having high stability to weak light (light having an intensity of less than 1 mW/cm$^2$ at 360 nm to 500 nm), such as ambient light, and completing polymerization in a remarkably short time when irradiated with active light (the intensity at the above-described wavelength region being about 100 mW/cm$^2$ or higher) by a light irradiator that is generally used for polymerization and curing, such as a halogen lamp, a xenon lamp, or a laser diode, thus producing a cured product having satisfactory physical properties; and to provide a dental filling restorative material formed from this composition.

Means for Solving the Problems

In view of the problems described above, the inventors of the present invention continuously conducted a thorough investigation. As a result, the inventors found that a curable composition that includes a spherical filler having a particular average particle size and a particular particle size distribution and is obtainable by combining the spherical filler with a spherical filler having a higher refractive index than a polymer of a polymerizable monomer, exhibits excellent color tone adaptability to natural teeth, and thus one of the problems described above can be solved. Furthermore, the inventors found that the above-mentioned curable composition including a photopolymerization initiator formed by including a photosensitizing compound, a tertiary amine compound, and a photoacid generator, has increased sensitivity to an irradiator equipped with a halogen lamp, a xenon lamp, or a laser diode (sensitivity to active light), and thus the curing rate is increased. Furthermore, even if the amount of the photosensitizing compound is decreased by such an increase in the curing rate, polymerization activity (curing rate) of the same extent as conventional cases can be obtained, and by reducing the amount of the photosensitizing compound, the environmental photostability can be enhanced while the polymerization activity under active light is maintained. Therefore, the inventors found that the problems described above can all be solved, and thus completed the present invention.

That is, the photocurable composition of the present invention contains a polymerizable monomer (A); a spherical filler (B) having an average particle size in the range of 230 nm to 1,000 nm; and a polymerization initiator (C), in which 90% or more of the individual particles constituting the spherical filler (B) are present in the range of 5% greater or less than the average particle size, the polymerizable monomer (A) and the spherical filler (B) satisfy condition (X1) represented by the following Formula (1):

$$nP < nF \quad (1)$$

in which nP represents the refractive index at 25° C. of a polymer obtainable by polymerizing the polymerizable monomer (A); and nF represents the refractive index at 25° C. of the spherical filler (B), and
the polymerization initiator (C) includes a photosensitizing compound (C1), a tertiary amine compound (C2), and a photoacid generator (C3).

According to a preferred example of the present invention, an aryliodonium salt-based compound is included therein as the photoacid generator (C3).

According to a more preferred example of the present invention, an aryliodonium salt-based compound that produces, by a cleavage reaction, an acid having an acid dissociation constant in water at 25° C. of −3.0 or higher is included as the photoacid generator (C3).

According to another preferred example of the present invention, an s-triazine compound having a trihalomethyl group as a substituent is included as the photoacid generator (C3).

According to another preferred example of the present invention, an s-triazine compound having a trihalomethyl group as a substituent is included as the photoacid generator (C3), and an aromatic tertiary amine compound and an aliphatic tertiary amine compound are respectively included as the tertiary amine compound (C2).

In order to obtain superior color tone adaptability to natural teeth, the difference between the refractive index nF at 25° C. of the spherical filler (B) and the refractive index nP at 25° C. of a polymer obtained by polymerizing the polymerizable monomer (A) is preferably 0.001 or more, more preferably 0.002 or more, and even more preferably 0.005 or more.

According to a preferred example of the present invention, a plurality of (meth)acrylic compounds are included as the polymerizable monomer (A), and the refractive index of the polymerizable monomer (A) at 25° C. is in the range of 1.38 to 1.55.

According to another preferred example of the present invention, the spherical filler (B) is spherical silica/titanium oxide-based composite oxide particles, and the refractive index thereof at 25° C. is in the range of 1.45 to 1.58.

The dental filling restorative material of the present invention is formed from the photocurable composition described above.

In regard to the dental filling restorative material, it is preferable that the average particle size of the spherical filler (B) is in the range of 230 nm to 500 nm. This dental filling restorative material is suitable for the restoration of a cavity in which the dentine is positioned at the surface of the deep part.

The average particle size of the spherical filler (B) is more preferably in the range of 260 nm to 350 nm. This dental filling restorative material is suitable for the restoration of a cavity in which the dentine is a part having a brown-reddish color tone.

Effects of the Invention

The photocurable composition of the present invention and a dental filling restorative material using this composition have satisfactory cavity restoration workability for the restoration of a tooth, particularly for a cavity including the dentine in the deep part, and enable restoration by which the external appearance of a cured product formed therefrom matches the appearance of natural teeth, while the match of the appearance with natural teeth is sustained for a long time period. Furthermore, since the photocurable composition and the dental filling restorative material are stable to weak light such as ambient light, the photocurable composition and the dental filling restorative material do not cure at the time of operations such as filling and building up, and since polymerization is completed in a remarkably short time by irradiation with strong light emitted by an irradiator such as a halogen lamp, a xenon lamp, or a laser diode, the restoration operation can be completed rapidly without imposing a burden on the patient. A cured product obtained therefrom has high mechanical strength and can be suitably used as a dental filling restorative material.

PREFERRED MODE FOR CARRYING OUT THE INVENTION

The photocurable composition of the present invention contains a polymerizable monomer (A); a spherical filler (B) having an average particle size in the range of 230 nm to 1,000 nm; and a polymerization initiator (C). Furthermore, the polymerization initiator (C) includes a photosensitizing compound (C1) a tertiary amine compound (C2), and a photoacid generator (C3).

The photocurable composition of the present invention has a feature of having particular color tone behavior. When measurement is made for the photocurable composition in a state of having formed a cured product, having a thickness of 1 mm, using a color difference meter, it is preferable that the value (V) of the colorimetric values of the colored light according to the Munsell Color System on a black background (backing having a value (V) of 1 according to the Munsell Color System) is less than 5 while the chroma (C) is 0.05 or greater, and the value (V) of the colorimetric values of the colored light according to the Munsell Color System on a white background (backing having a value (V) of 9.5 according to the Munsell Color System) is 6 or greater while the chroma (C) is less than 2. The value of the colored light on a black background is preferably 4.5 or less, and more preferably 4.0 or less. The chroma (C) of the colored light on a black background is preferably 0.07 or greater, and more preferably 0.09 or greater. The value (V) of the colored light on a white background is preferably 6.5 or greater, and more preferably 7.0 or greater. The chroma (C) of the colored light on a white background is preferably 1.5 or less, and more preferably 1.2 or less.

Since the average particle size of the spherical filler (B) included in the composition is 230 nm to 1,000 nm, the colored light on a black background is yellowish to reddish. Specifically, the hue (H) of the colorimetric values obtained by measuring the colored light according to the Munsell Color System is in the range of 0 P or greater and less than 10 P, 0 RP or greater and less than 10 RP, 0 R or greater and less than 10 R, 0 YR or greater and less than 10 YR, 0 Y or greater and less than 10 Y, or 0 GY or greater and less than 10 GY. Preferably, the hue (H) is in the range of 0 P or greater and less than 10 P, 0 RP or greater and less than 10 RP, 0 R or greater and less than 10 R, 0 YR or greater and less than 10 YR, or 0 Y or greater and less than 10 Y; and more preferably in the range of 0 RP or greater and less than 10 RP, 0 R or greater and less than 10 R, 0 YR or greater and less than 10 YR, or 0 Y or greater and less than 10 Y.

For example, by using the spherical filler (B) described above, a cured product that gives out a colored light having a reddish hue on a black background is such that, as long as the environment is an environment in which the periphery of the cured product exhibits a reddish color, even if the environment changes into various colors ranging from red-yellow color to red-brown color, the cured product satisfactorily matches the environment in all of the value, chroma, and hue. Specifically, in a case in which the chromaticity (hue and chroma) of the background (backing environment) is high, external light such as radiated light is absorbed by a background having high chromaticity, and light other than the colored light given out by the cured product is suppressed. Therefore, an observation of the colored light can be made. On the other hand, in a case in which the chromaticity of teeth on the background (backing environment) is low, external light such as radiated light is scattered at the background of low chromaticity, and since the scattered light is stronger than the colored light given out by the cured product, the colored light is canceled and is attenuated. Therefore, in regard to the cured product of the photocurable composition of the present invention, a strong colored light is given out in a backing environment with high chromaticity, and a weak colored light is given out in a backing environment with low chromaticity. Therefore, an effect in which the colored light matches a wide range of reddish colors of various surrounding environments is exhibited.

A photocurable composition that exhibits such unique color tone behavior is obtained by using a spherical filler (B) having a particular average particle size and a narrow particle size distribution, which will be explained below, and by selecting a polymerizable monomer and a spherical filler (B) that satisfy condition (X1) represented by the following Formula (1):

$$nP<nF \quad (1)$$

in which nP represents the refractive index at 25° C. of a polymer obtainable by polymerizing the polymerizable monomer (A); and nF represents the refractive index at 25° C. of the spherical filler (B).

It is important that the average particle size of the spherical filler (B) is 230 nm to 1,000 nm, and 90% (based on number) or more of the individual particles constituting the spherical filler (B) are present in the range of 5% greater or less than the average particle size. That is, it is implied that a large number of primary particles constitute the spherical filler (B), and in the range of 5% greater or less than the average particle size (when the value of the average particle size is designated as 100%, the particle size range of ±5% of that value) of the large number of primary particles, 90% or more of the number of primary particles are present in the total number of primary particles. This proportion is preferably 91% or higher, and more preferably 93% or higher. A colored light exhibiting a structural color that is expressed by interference, diffraction, refraction, scattering, or the like (hereinafter, simply referred to as "interference, scattering, or the like"), is expressed when diffraction and interference occur according to Bragg's conditions, and light having a particular wavelength is emphasized, or light other than a light having a particular wavelength is scattered so that only the light having a particular wavelength is reflected. Thus, when a spherical filler having the above-mentioned average particle size and particle size distribution is incorporated, a cured product of the photocurable composition exhibits a yellowish to reddish colored light according to the average particle size of the spherical filler. From the viewpoint of further enhancing the effect of expressing colored light by interference, scattering, or the like, the average particle size of the spherical filler is preferably in the range of 230 nm to 800 nm, more preferably in the range of 230 nm to 500 nm, even more preferably in the range of 230 nm to 350 nm, and particularly preferably in the range of 260 nm to 350 nm. In a case in which a spherical filler having an average particle size smaller than 230 nm is used, bluish coloration occurs, and the coloration does not match the color tone of the dentine. On the other hand, when a spherical filler having an average particle size of larger than 1,000 nm is used, expression of interference, scattering, or the like of light can be expected; however, since problems such as settling of the spherical filler and deterioration of abradability occur, the resulting photocurable composition is not preferable as a dental filling restorative material.

The photocurable composition of the present invention exhibits a yellowish to reddish colored light depending on the average particle size of 230 nm to 1,000 nm of the spherical filler (B). As explained above, in regard to the crown part, the dentine is positioned in most of the deep part of a restored cavity except for the incisal part, the dentine has high value and high chroma and has a yellowish to reddish hue (particularly reddish hue ranging from red-yellow to red-brown), and the variation depending on individual differences and site differences is large. Therefore, in the case of restoring such a cavity in which the surface of the deep part is positioned at the dentine, it has been hitherto especially difficult to adapt the color tone. The deep part of a restored cavity means the cavity floor of the restored cavity and the sidewall part in the lower part than the surface layer where enamel is located in this regard, when the photocurable composition of the present invention in which a spherical filler (B) having the above-mentioned average particle size and particle size distribution has been incorporated is used, the yellowish to reddish structural color described above is expressed, the structural color satisfactorily matches the color tone of dentine in the background, and thus a restored part having excellent adaptability to the tooth after restoration is obtained. On the other hand, in a case in which a spherical filler having an average particle size in the range of 150 nm or more and less than 230 nm is used, the colored light thus obtainable is bluish and does not match the color tone of the dentinal surface at the deep part.

As such, when the photocurable composition of the present invention is used, a colored light caused by interference, scattering, or the like of light can be clearly recognized, and a filling restorative material that can form a restored site having an external appearance close to that of natural teeth can be obtained without using a pigment, a dye, or the like. In an area where a structural color is produced by interference of light, it is considered that the relation between the particle size of the spherical filler and the interference phenomenon of light is dependent on the Bragg's diffraction conditions.

There are individual differences in the color tone of natural teeth, and the color tone may vary depending on the site to be restored; however, the photocurable composition of the present invention that utilizes the phenomenon of interference, scattering, or the like of light can cope with various color tones. Specifically, in a case in which the chromaticity (hue and chroma) of the tooth as a background (backing) is high, external light such as radiated light is absorbed by the background having high chromaticity, and light other than the colored light (interference light, scattered and reflected light, or the like) given out from a cured product of the photocurable composition that utilizes the phenomenon of interference, scattering, or the like of light, is suppressed. Therefore, an observation of colored light can be made. On the other hand, in a case in which the chromaticity of the tooth as a background (backing) is low, external light such as radiated light is scattered at the background having low chromaticity, and since the scattered light is stronger than the colored light (interference light, scattered and reflected light, or the like) given out by a cured product of the photocurable composition that utilizes the phenomenon such as interference, scattering, or the like of light, the colored light is canceled and attenuated.

As explained above, a strong colored light is given out with respect to a natural tooth having high chromaticity, and a weak colored light is given out with respect to a tooth having low chromaticity. Therefore, the photocurable composition of the present invention has a wide range of color tones that can be covered by a single kind of paste, and wide color tone adaptability is obtained with pastes of fewer colors than conventional pastes. As such, adapting to the color tone of natural teeth with pastes of fewer colors without depending on the magnitude of chromaticity, is not easily achieved by conventional pastes that are adjusted by mixing of coloring substances such as pigments.

The photocurable composition of the present invention has a feature that a colored light is produced by the phenomenon of interference, scattering, or the like, and whether the colored light will be given out can be checked by measuring the spectral reflectance characteristics using a color difference meter under the conditions of both on a black background and on a white background. On a black background, when the above-mentioned conditions are satisfied, a characteristic reflection visible spectrum corresponding to the colored light is clearly recognized; however, on a white background, the photocurable composition shows a substantially uniform reflectance substantially over the whole range of visible light (380 nm to 780 nm). Thus, a particular reflection visible spectrum is not recognized, and the photocurable composition is substantially colorless. This is speculated to be because external light (for example, C light source or D65 light source) is absorbed or blocked on a black background, and a colored light caused by interference, scattering, or the like is emphasized; whereas on a white background, since scattered light of external light is strong, a colored light caused by interference, scattering or the like is not easily observed.

In order to obtain the effects of the present invention, it is important that the relation between the refractive index nP at 25° C. of a polymer obtained by polymerizing the polymerizable monomer (A) and the refractive index nF at 25° C. of the spherical filler (B) satisfy condition (X1) represented by the following Formula (1).

$$nP<nF \quad (1)$$

As shown by Formula (1), in regard to the photocurable composition of the present invention, the relation between the refractive indices of a polymer obtained by polymerizing the polymerizable monomer (A) and the spherical filler (B) is such that nP<nF. In a case in which the refractive index of the spherical filler (B) is high and the refractive index of the polymer as a matrix is low, a colored light produced by interference, scattering, or the like is strongly expressed; however, in an opposite case, light having short wavelengths are more easily subjected to interference or scattering, a colored light thus obtainable has shorter wavelengths and have bluish tint, and the color tone adaptability to restoration sites of various color tones is likely to become poor.

Hereinafter, the various components of the photocurable composition of the present invention will be explained.

<Polymerizable Monomer (A)>

Regarding the polymerizable monomer, any known monomer can be used without particular limitations. In the aspect of dental applications, from the viewpoint of the polymerization rate, a radical polymerizable or cationic polymerizable monomer is preferred. Particularly preferred examples of the radical polymerizable monomer include a (meth)acrylic compound. Examples of the (meth)acrylic compound include (meth)acrylates given below. Furthermore, particularly preferred examples of the cationic polymerizable monomer include epoxies and oxetanes.

Generally, examples of the (meth)acrylates that are suitably used include the compounds listed under the following items (I) to (III).

(I) Bifunctional Polymerizable Monomers
(i) Aromatic Compound-Based Monomers
2,2-bis(methacryloyloxyphenyl)propane,
2,2-bis[(3-methacryloyloxy-2-hydroxypropyloxy)phenyl] propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane, 2(4-methacryloyloxydiethoxyphenyl)-2(4-methacryloyloxytriethoxyphenyl)propane,
2(4-methacryloyloxydipropoxyphenyl)-2-(4-methacryloyloxytriethoxyphenyl)propane,
2,2-bis(4-methacryloyloxypropoxyphenyl)propane,
2,2-bis(4-methacryloyloxyisopropoxyphenyl)propane,
and acrylates corresponding to these methacrylates; diadducts obtainable from adducts of vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds having an aromatic group, such as diisocyanatomethylbenzene and 4,4'-diphenylmethane diisocyanate; and the like.

(ii) Aliphatic Compound-Based Monomers
ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-dimethacrylate,
and acrylates corresponding to these methacrylates; diadducts obtainable from adducts between vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds such as hexamethylene diisocyanate, trimethylhexamethylene diisocyanate, and diisocyanatomethylcyclohexane, isophorone diisocyanate, and methylenebis(4-cyclohexyl isocyanate), for example, 1,6-bis(methacrylethyloxycarbonylamino)trimethylhexane; 1,2-bis(3-methacryloyloxy-2-hydroxypropoxy)ethyl, and the like.

(II) Trifunctional Polymerizable Monomers
trimethylolpropane trimethacrylate,
trimethylolethane trimethacrylate,
pentaerythritol trimethacrylate, and
trimethylolethane trimethacrylate, and the like
And acrylates corresponding to these methacrylates, and the like.

(III) Tetrafunctional Polymerizable Monomers
pentaerythritol tetramethacrylate,
pentaerythritol tetraacrylate;
diadducts obtainable from adducts between diisocyanate compounds such as diisocyanatomethylbenzene, diisocyanatomethylcyclohexane, isophorone diisocyanate, hexamethylene diisocyanate, trimethylhexamethylene diisocyanate, methylenebis(4-cyclohexyl isocyanate), 4,4-diphenylmethane diisocyanate, and tolylene-2,4-diisocyanate, and glycidol dimethacrylate, and the like.

Regarding these polyfunctional (meth)acrylate-based polymerizable monomers, a plurality of kinds of compounds may be used in combination as necessary.

Furthermore, if necessary, monofunctional (meth)acrylate-based monomers, such as methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates; and polymerizable monomers other than the above-mentioned (meth)acrylate-based monomers may also be used.

According to the present invention, as the polymerizable monomer (A), generally, a plurality of polymerizable monomers is used for the purpose of regulating the physical properties of the cured product (mechanical characteristics and adhesiveness to dentine); however, at this time, it is desirable that the types and the mixing ratio of the monomers are set such that the refractive index at 25° C. of the polymerizable monomer (A) is in the range of 1.38 to 1.55. That is, by setting the refractive index of the polymerizable monomer (A) to be in the range of 1.38 to 1.55, the refractive index nP at 25° C. of a polymer obtainable from the polymerizable monomer (A) can be set to be approximately in the range of 1.40 to 1.57. There are cases of using a plurality of kinds of polymerizable monomers; however, regarding the refractive index in this case, it is acceptable as long as the refractive index of the mixture of a plurality of polymerizable monomers is in the above-mentioned range, and the refractive indices of the individual polymerizable monomers may not be necessarily in the range described above.

The refractive indices of a polymerizable monomer and a polymer thereof can be determined at 25° C. using an Abbe refractometer.

<Spherical Filler (B)>

A general photocurable composition includes various filler materials such as inorganic fillers, organic fillers, and organic-inorganic composite fillers; however, in the photocurable composition of the present invention, a spherical filler (B) having an average particle size of 230 nm to 1,000 nm, for the purpose of expressing a colored light caused by interference, scattering, or the like is incorporated. A feature of the photocurable composition of the present invention is that the photocurable composition includes a spherical filler (B) that is spherical in shape and has a narrow particle size distribution. A colored light caused by interference is produced at an area where constituent particles are relatively regularly accumulated, and a colored light caused by scattering is produced at an area where constituent particles are disorderly dispersed. The spherical filler (B) that constitutes the photocurable composition of the present invention is spherical in shape and has a narrow particle size distribution, and therefore, colored light caused by interference, scattering, or the like is produced. On the other hand, when irregularly shaped particles that are produced by pulverization or the like are used, the particle size distribution is broad, and the shape is also non-uniform. Therefore, the particles are not regularly accumulated, and colored light is not produced.

The phrase "spherical filler is relatively regularly accumulated" as used in the present specification means a state which the spherical filler is uniformly dispersed in the polymerizable monomer, and the filler particles are arranged in an isotropic structure with certain orderliness.

Regarding the spherical filler (B), any filler that is used as a component of a general photocurable composition in the field of dentistry can be used without limitations as long as the requirements for the average particle size and the particle size distribution as described below are satisfied. Specific examples include inorganic fillers such as amorphous silica, silica-titanium group oxide-based composite oxide particles (silica-zirconia, silica-titania, and the like), quartz, alumina, barium glass, zirconia, titania, lanthanoids, and colloidal silica. Furthermore, the spherical filler (B) may also be an organic filler or an organic-inorganic composite filler.

Among these, silica-titanium group oxide-based composite oxide particles are preferred from the viewpoint that the refractive index is easily adjustable.

As described above, the average particle size of the spherical filler (B) is 230 nm to 1,000 nm, and depending on the particle size, a cured product of the photocurable composition exhibits a yellowish to reddish colored light. Among these, when a spherical filler having an average particle size in the range of 230 nm to 260 nm is used, the colored light thus obtainable is yellowish, and the photocurable composition is useful for the restoration of a cavity in which the color tone of the tooth flank in the periphery of the restored tooth is in the class of B system (red-yellow) according to Shade Guide "VITAPAN Classical (registered trademark)". When a spherical filler having an average particle size in the range of 260 nm to 350 nm is used, the colored light thus obtainable is reddish, and the curable composition is useful for the restoration of a cavity in which the color one of the tooth flank in the periphery of the restored tooth is in the class of A system (red-brown) according to Shade Guide "VITAPAN Classical (registered trademark)". Since the hue of the dentine is reddish as such in many cases, in the present invention, it is preferable to use a spherical filler having an average particle size in the range of 230 nm to 350 nm, from the viewpoint that adaptability to restored teeth having a variety of color tones is improved to a large extent, and it is more preferable to use a spherical filler having an average particle size in the range of 260 nm to 350 nm, from the viewpoint that adaptability is further improved.

According to the present specification, the average particle size of the spherical filler (B) is obtained by taking a photograph of the powder by scanning electron microscopy, measuring the number of whole particles (30 particles or more) that are observed within a unit viewing field of the photograph and the primary particle size (maximum diameter) of the whole particles, and calculating average values by the following formula based on the measurement, values thus obtained.

$$\bar{x} = \frac{\sum_{i=1}^{n} x_i}{n} \text{(Number average)}$$

($n$: number of particle, $x_i$: primary particle size (maximum diameter) of $i$-th particle)

According to the present specification, regarding the proportion (%) of particles in the range of the average particle size ±5% of the spherical filler (B), the number of particles having a primary particle size (maximum diameter) that is not in the particle size range of the average particle size ±5% determined as described above, among the whole particles (30 particles or more) within a unit viewing field of the above-mentioned photograph, is measured, the value is subtracted from the number of whole particles, the number of particles in the particle size range of average particle size ±5% within a unit viewing field of the photograph is determined, and the proportion of particles in the range of the average particle size ±5% is calculated by the following formula.

Proportion (%) of particles in the range of average particle size ±5% of spherical filler (B)=[(number of particles in the particle size range of average particle size ±5% within a unit viewing field of scanning electron microscopic photograph)/(number of whole particles within a unit viewing field of scanning electron microscopic photograph)]×100

Here, the spherical shape of the spherical filler (B) may be an approximate spherical shape, and the shape is not necessarily essential to be a perfect true sphere. Generally, when a photograph of particles is taken with a scanning electron microscope, and for each of the particles (30 particles or more) within a unit viewing field of the photograph, when the average uniformity ratio is calculated by dividing the particle size in a direction perpendicular to the maximum diameter by the maximum diameter, it is acceptable as long as the average uniformity ratio is 0.6 or greater, and more preferably 0.8 or greater.

Furthermore, in order to obtain colored light, it is desirable that the average particle size and the particle size distribution of the spherical filler (B) are in the above-mentioned ranges, and the spherical filler (B) may be incorporated, in a state in which the spherical filler (B) constitute a composite filler with an organic resin matrix, into the photocurable composition of the present invention.

In regard to the composite filler, for the organic resin matrix, a homopolymer or a plurality of copolymers obtainable by using the same polymerizable monomers as those described as the polymerizable monomer (A) mentioned above, can be used without any limitations. However, the relation between the refractive index nD at 25° C. of the organic resin matrix and the refractive index nF at 25° C. of the spherical filler (B) needs to satisfy condition represented by the following Formula. (2).

$$nD < nF \qquad (2)$$

The refractive index difference between the refractive index nD at 25° C. of the organic resin matrix and the refractive index nP at 25° C. of a polymer obtained by polymerizing the polymerizable monomer (A) is preferably 0.005 or less, from the viewpoint of transparency of a cured product thus obtainable. By adjusting the refractive index difference to be 0.005 or less, transparency is enhanced, and attenuation of a colored light caused by interference tends to be suppressed.

The average particle size of the composite filler is not particularly limited; however, from the viewpoint of improving the mechanical strength of the cured product or the operability of the curable paste, the average particle size is preferably 2 μm to 100 μm. Furthermore, the shape of the composite filler is not particularly limited. For example, an irregularly shaped composite filler obtainable by mixing predetermined amounts of various components of the spherical filler (B), the polymerizable monomer, and the polymerization initiator, performing polymerization by methods such as heating and light irradiation, and then pulverizing the resultant product, may be used. Alternatively, a spherical or an approximately spherical composite filler, which is produced according to the method described in WO 2011/115007 or WO 2013/039169, may also be used.

The silica-titanium group oxide-based composite oxide particles according to the present specification are composite oxide of silica and a titanium group (elements of Group IV in the Periodic Table of Elements) oxide, and examples include silica-titanic, silica-zirconia, and silica-titania-zirconia. Among these, silica-zirconia is preferred since the refractive index of the filler is adjustable, and high X-ray opacity can also be imparted. The composite ratio is not particularly limited; however, from the viewpoint of imparting sufficient X-ray opacity and adjusting the refractive index to a suitable range that will be described below, it is preferable that the content of silica is 70 mol % to 95 mol %, and the content of the titanium group oxide is 5 mol % to 30 mol %. In the case of silica-zirconia, the refractive index can be freely varied by varying the respective composite ratio as such.

Meanwhile, in these silica-titanium group oxide-based composite oxide particles, incorporation of metal oxides other than silica and titanium group oxides is also allowed, as long as the amount is small. Specifically, an alkali metal oxide such as sodium oxide or lithium oxide may be incorporated in an amount of 10 mol % or less.

A method for producing such silica-titanium group oxide-based composite oxide particles not particularly limited; however, in order to obtain the particular spherical filler of the present invention, for example, a so-called sol-gel method of adding a mixed solution including a hydrolyzable organosilicon compound and a hydrolyzable organotitanium group metal compound to an alkaline solvent, performing hydrolysis, and precipitating a reaction product, is suitably employed.

These silica-titanium group oxide-based composite oxide particles may be surface-treated with a silane coupling agent. As a result of surface treatment using a silane coupling agent, particles having excellent interfacial strength between the silica-titanium group oxide-based composite oxide particles and the polymer portion of the polymerizable monomer (A) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be determined after the mechanical properties and the like of a curable composition thus obtainable are checked in advance by experiments. However, an example of a suitable range is the range of 0.1 parts by mass to 15 parts by mass with respect to 100 parts by mass of the particles.

As explained above, a colored light caused by interference, scattering, or the like, which exhibits satisfactory color tone adaptability to natural teeth, is obtained in a case in which condition (X1) represented by the following Formula (1) is satisfied:

$$nP < nF \qquad (1)$$

in which nP represents the refractive index at 25° C. of a polymer obtainable by polymerizing the polymerizable monomer (A); and nF represents the refractive index at 25° C. of the spherical filler (B).

That is, the refractive index of the spherical filler (B) is in a state of being higher than the refractive index of a polymer obtainable by polymerizing the polymerizable monomer (A). The difference between the refractive index nF (25° C.) of the spherical filler (B) and the refractive index nP (25° C.) of a polymer obtained by polymerizing the polymerizable monomer (A) is preferably 0.001 or more, more preferably 0.002 or more, and even more preferably 0.005 or more. In regard to the refractive index, since the refractive index is clearly expressed in a case in which the cured product has high transparency, regarding the spherical filler (B), it is preferable to select and use a spherical filler which has a refractive index that differs from the refractive index of a polymer obtained by polymerizing the polymerizable monomer (A) by 0.1 or less, and more preferably 0.05 or less, and which does not impair transparency as far as possible.

Furthermore, in a case in which the spherical filler (B) constitutes a composite filler with an organic resin matrix, in order to obtain satisfactory color one adaptability to natural teeth, it is necessary for the spherical filler to satisfy condition (X2) represented by the following Formula (2):

$$nD < nF \quad (2)$$

in which nD represents the refractive index at 25° C. of the organic resin matrix; and nF represents the refractive index at 25° C. of the spherical filler (B).

That is, the refractive index of the spherical filler (B) is in a state of being higher than the refractive index of the organic resin matrix. The difference between the refractive index nF (25° C.) of the spherical filler (B) and the refractive index nD (25° C.) of the organic resin matrix is preferably 0.001 or more, more preferably 0.002 or more, and even more preferably 0.005 or more. In regard to the refractive index, since the refractive index is clearly expressed in a case in which the cured product has high transparency, regarding the spherical filler (B), it is preferable to select and use a spherical filler which has a refractive index that differs from the refractive index of the organic resin matrix is 0.1 or less, and more preferably 0.05 or less, and which does not impair transparency as far as possible.

The incorporation amount of the spherical filler (B) according to the present invention is preferably 50 parts by mass to 1,500 parts by mass with respect to 100 parts by mass of the polymerizable monomer (A). When the spherical filler (B) is incorporated in an amount of 50 parts by mass or more, a colored light caused by interference, scattering, or the like is satisfactorily expressed. Furthermore, in a case in which a spherical filler (B) having a refractive index that differs from the refractive index of a polymer obtained by polymerizing the polymerizable monomer (A) by more than 0.1, there is a risk that the transparency of the cured product may be deteriorated, and the effect of expressing colored light may not be sufficiently exhibited. In consideration of these, the incorporation amount of the spherical filler (B) is more preferably 100 parts by mass to 1,500 parts by mass, and even more preferably 150 parts by mass to 1,500 parts by mass, with respect to 100 parts by mass of the polymerizable monomer (A).

In the spherical filler (B), the refractive index of the silica-based filler, particularly the silica-titanium group oxide-based composite oxide, is in the range of about 1.45 to 1.58 according to the content of silica component. That is, by setting the refractive index of the polymerizable monomer to the above-described range (1.38 to 1.55), the spherical filler (B) can be easily selected so as to satisfy the above-mentioned condition (X1). That is, a silica-titanium group oxide-based composite oxide (for example, silica-titania or silica-zirconia) containing an appropriate amount of silica component may be used.

<Polymerization Initiator (C)>

The polymerization initiator (C) used for the present invention includes a photosensitizing compound (C1), a tertiary amine compound (C2), and a photoacid generator (C3). In the following description, these various components will be explained.

(Photosensitizing Compound (C1))

The photosensitizing compound (C1) according to the present invention is a compound having a maximum absorption wavelength of 350 nm to 700 nm and having a function of producing, for example, an active species effective for polymerization, such as a radical. The active species is usually produced as a result of energy transfer or electron transfer between the photosensitizing compound and a polymerizable monomer or another substance.

Regarding the photosensitizing compound (C1), any known photosensitizing compound is used without any limitation. Examples of the photosensitizing compound that is suitably used for the present invention include a ketone compound (particularly, an α-diketone compound), a coumarin-based coloring matter, a cyanine-based coloring matter, a merocyanine-based coloring matter, a thiazine-based coloring matter, an azine-based coloring matter, an acridine-based coloring matter, a xanthene-based coloring matter, a squarylium-based coloring matter, and a pyrylium salt-based coloring matter, and particularly, a ketone compound such as an α-diketone compound is preferred. Specific examples of the photosensitizing compound that is suitably used for the present invention include ketone compounds) such as camphorquinone, 9,10-phenanthrenequinone, benzil, diacetyl, acetylbenzoyl, 2,3-pentadione, 2,3-octadione, 4,4'-dimethoxybenzil, acenaphthenequinone, 4,4-bis(dimethylamino)benophenone, 9-fluorenone, 3,4-benzo-9-fluorenone, 2-dimethylamino-9-fluorenone, 2-methoxy-9-fluorenone, 2-chloro-9-fluorenone, 2,7-dichloro-9-fluorenone, 2-nitro-9-fluorenone, 2-acetoxy-9-fluorenone, benzanthrone, anthraquinone, and 2,4-dihydroxybenzophenone; coumarin-based coloring matters such as 3-thienoylcoumarin, 3-(4-methoxybenzoyl)coumarin, 3-(4-cyanobenzoyl)coumarin, 3-thienoyl-7-methoxycoumarin, 3-benzoyl-7-methoxycoumarin, 5,7-dimethoxy-3-(4-methoxybenzoyl)coumarin, 3-acetyl-7-dimethylaminocoumarin, 7-diethylamino-3-(4-cyanobenzoyl)coumarin, 7-diethylamino-3-(4-dimethylaminobenzoyl)coumarin, 3-cinnamoyl-7-diethylaminocoumarin, 3-carboxy-7-diethylaminocoumarin, 3-(4-carboxybenzoyl)-7-diethylaminocoumarin 3,3'-carbonylbis(7-diethylamino)coumarin, 2,3,6,7-tetrahydro-1,1,7,7-tetramethyl-10-(benzothiazoyl)-11-oxo-1H,5H,11H-[1]benzopyrano[6,7,8-ij]quinolidine, 3,3'-carbonylbis(5,7-)dimethoxy 3,3'-biscoumarin, 3-(2'-benzoxazoyl)-7-diethylaminocoumarin, 3-(5'-phenylthiazolyl-2')-7-diethylaminocoumarin, and 3,3'-carbonylbis(4-cyano-7-diethylamino)coumarin; cyanine-based coloring matters such as 1,3,3,1',3,3'-hexamethyl-2,2'-indocyanine perchlorate, 1,3'-diethyl-2,2'-quinoselenacyanine iodide, 1,1'-diethyl-2,4'-quinocyanine iodide, 3,3'-diethyl-2,2'-thiazolinocarbocyanine iodide, 3,3',9-triethyl-5,5'-diphenyl-2,2'-oxacarbocyanine iodide, 3,3'-diethyl-2,2'-thiacarbocyanine iodide, 1,1'-diethyl-2,4'-quinocarbocyanine iodide, 3,3'-diethyl-2,2'-oxadicarbocyanine iodide, 3,3'-diethyl-2,2'-(4,5,4',5'-dibenzo)thiadicarbocyanine iodide, and 3,3'-diethyl-2,2'-oxatricarbocyanine iodide; merocyanine-based coloring matters such as 3-ethyl-5-[2-(3-methyl-2-thiazolidinylidene)ethylidene]-2-thio-2,4-oxazolidinedione, 3-carboxymethyl 5-[2-(3-ethyl-2-benzothiazolinylidene)ethylidene]rhodanine, and 3-ethyl-5-[2-(3-ethyl-4-methyl-2-thiazolinylidene)ethylidene]rhodanine; thiazine-based coloring matters such as methylene blue and thionine chloride; azine-based coloring matters such as riboflavin and 1-amino-4-nitrophenazine; acridine-based coloring matters such as 1-aminoacridine, 9-(2'-hydroxystyry) acridine, Acryl Orange, and Acridine Yellow; xanthene-based coloring matters such as rhodamine, fluorescein, and Rose Bengal; squarylium-based coloring matters such as dihydro-3-[2-hydroxy-3-(5-isopropyl-3,8-dimethyl-1-azirenyl)-4-oxo-2-cyclobuten-1-ylidene]-7-isopropyl-1,4-dimethylazulenium hydroxide, and an internal salt; and pyrylium-based coloring matters such as triphenylpyrylium perchloriate and 2,6-bis (4-methylphenyl)-4-(4-phenylthiochloroperchlorate).

Among the above-described compounds, α-diketone compounds such as camphorquinone, 9,10-phenanthrenequinone, benzil, diacetyl, acetylbenzoyl, 2,3-pentadione, 2,3-octadione, 4,4'-dimethoxybenzil, and acenaphthenequinone are more preferred.

The use amount of the photosensitizing compound (C1) is not particularly limited; however, the use amount is usually 0.01 parts by mass to 10 parts by mass, preferably 0.03 parts by mass to 5 parts by mass, and more preferably 0.05 parts by mass to 2 parts by mass, with respect to 100 parts by mass or the polymerizable monomer (A).

(Tertiary Amine Compound (C2))

Regarding the tertiary amine compound (C2), any known tertiary amine compound can be used without any limitations, and from the viewpoint of foul odor or the like, an aromatic tertiary amine compound is preferred. Examples of the aromatic tertiary amine compound that is suitably used for the present invention include N,N-dimethylaniline, N,N-dibenzylaniline, N,N-dimethyl-p-toluidine, N,N-diethyl-p-toluidine, N,N-di(β-hydroxyethyl)-p-toluidine, methyl p-dimethylaminobenzoate, ethyl p-dimethylaminobenzoate, and amyl p-dimethylaminobenzoate.

Furthermore, as the tertiary amine compound (C2), an aliphatic tertiary amine compound may also be used. Specific examples of the aliphatic tertiary amine compound that is suitably used for the present invention include triethanolamine, N-methyldiethanolamine, triethylamine, tributylamine, N,N-dimethylaminoethyl methacrylate, and N,N-diethylaminoethyl methacrylate.

Any of these tertiary amine compounds may be used, and a tertiary amine compound of different kind may be used in combination therewith; however, at is preferable to use at least one aromatic tertiary amine compound.

The use amount of the tertiary amine compound (C2) is not particularly limited; however, the use amount is usually 10 parts by mass to 1,000 parts by mass, preferably 50 parts by mass to 500 parts by mass, and more preferably 70 parts by mass to 300 parts by mass, with respect to 100 parts by mass of the photosensitizing compound (C1). Furthermore, the use amount of the tertiary amine compound (C2) is preferably 0.01 parts by mass to 10 parts by mass, more preferably 0.02 parts by mass to 5 parts by mass, and even more preferably 0.05 parts by mass to 3 parts by mass, with respect to 100 parts by mass of the polymerizable monomer (A).

(Photo-Acid Generator (C3))

Regarding the photoacid generator (C3), any known photoacid generator is used without any limitations. Examples of the photoacid generator that is suitably used for the present invention include an aryliodonium salt-based compound, a sulfonium salt-based compound, a sulfonic acid ester compound, an s-triazine compound having a halomethyl group as a substituent, and a pyridinium salt-based compound, and it is particularly preferable that the photoacid generator is an aryliodonium salt-based compound or an s-triazine compound having a halomethyl group. Among aryliodonium salt-based compounds, a particularly preferred example of the photoacid generator (C3) according to the present invention is an aryliodonium salt that produces, by a cleavage reaction, an acid having an acid dissociation constant in water at 25'C of −3.0 or higher. From an aryliodonium salt, an acid (HX) is generated as represented by the following Formula (1) by a cleavage reaction by light irradiation.

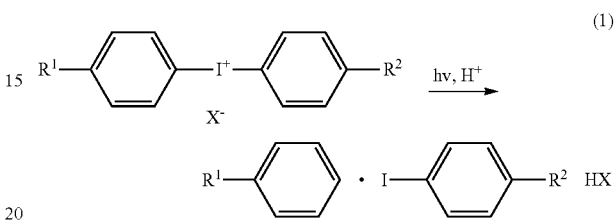

In Formula (1), $R^1$ and $R^2$ each independently represent a hydrogen atom or an alkyl group. Furthermore, $X^-$ represents a counteranion of an aryliodonium salt; and HX represents an acid generated in the cleavage reaction represented by Formula (1) described above.

A photopolymerization initiator including a photosensitizing compound, a tertiary amine compound, and an aryliodonium salt initiates a polymerization reaction as described in the following Formula (2) when irradiated with active light, and generates an acid derived from the counteranions of an aryl radical and an aryliodonium salt (see, for example, Non-Patent Document 8).

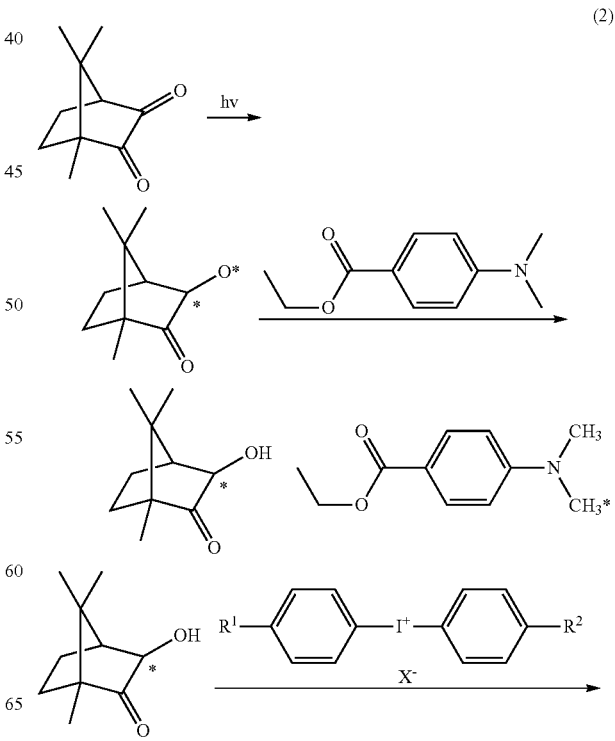

-continued

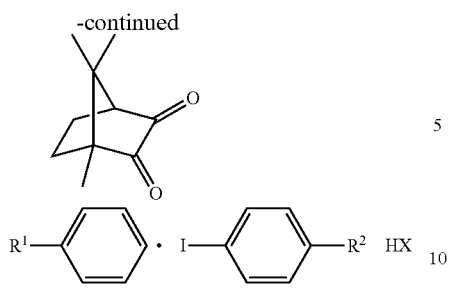

Here, since the acidity of the acid thus generated is higher, the activity of cationic polymerization is higher. For example, in Patent Document 7, an Example of using a diphenyliodonium hexafluorophosphate that generates an acid having high acidity is described. On the other hand, in a case of using an aryliodonium salt that generates an acid having high acidity, when an amine compound, particularly a tertiary amine compound, is present in the polymerization initiator, since the acid is likely to cause a polymerization reaction with the tertiary amine compound and produce a salt, it is considered that the polymerization activity may be damaged. For the polymerization initiator (C) of the present invention, it is preferable to use an aryliodonium salt that produces an acid by a cleavage reaction represented by Formula (1), the acid having an acid dissociation constant in water a 25° C. of −3.0 or higher, as the photoacid generator (C3). Furthermore, it is more preferable to use an aryliodonium salt that produces an acid by a cleavage reaction, the acid having an acid dissociation constant in water at 25° C. of −2.0 to 10.0.

When the acid dissociation constants of various acids in water at 25° C. are shown for reference, HCl (−3.7), HBr. (−4.1), $HNO_3$ (−1.8), chloroacetic acid (2.9), benzoic acid (4.2), and phenol (9.9) (see, for example, Non-Patent Document 9).

Specific examples of the aryliodonium salt that is suitably used for the present invention and produces an acid by a cleavage reaction, the acid having an acid dissociation constant in water at 25° C. of −3.0 or higher, include salts formed from cations such as diphenyliodonium, bis(p-chlorophenyl)iodonium, ditolyliodonium, bis(p-methoxyphenyl)iodonium, bis(p-tert-butylphenyl)iodonium, p-isopropylphenyl-p-methylphenyliodonium, bis(m-nitrophenyl)iodonium, p-tert-butylphenylphenyliodonium, p-methoxyphenylphenyliodonium, p-octyloxyphenyphenyliodonium, and p-phenoxyphenylphenyliodonium, and anions such as nitrate, acetate, chloroacetate, carboxylate, and phenolate.

Furthermore, among the aryliodonium salts described above, from the viewpoint of being easily available and having excellent polymerization activity, diphenyliodonium 2-carboxylate monohydrate is particularly preferred.

The aryliodonium salts described may be used singly or as mixtures of two or more kinds thereof.

Furthermore, as another particularly preferred example according to the present invention, among s-triazine compounds having a halomethyl group, an s-triazine compound having a trihalomethyl group as a substituent (hereinafter, also simply referred to as triazine compound) being included as the photoacid generator (C3) may be mentioned.

As the triazine compound, as long as it is an s-triazine compound having at least one trihalomethyl group such as a trichloromethyl group or a tribromomethyl group, any known compound can be used without any limitations. A particularly preferred triazine compound is represented by, for example, the following General Formula (3):

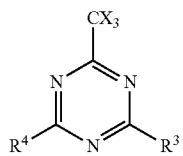

(3)

In General Formula (3), $R^3$ and $R^4$ each represent an organic group having an unsaturated bond conjugatable with a triazine ring, an alkyl group, or an alkoxy group; and X represents a halogen atom.

In General Formula (3), the halogen atom represented by X may be any of chlorine, bromine, and iodine; however, chlorine is generally used. Therefore, the substituent ($CX_3$) bonded to the triazine ring is generally a trichloromethyl group.

$R^3$ and $R^4$ may each represent any of an organic group having an unsaturated bond conjugatable with a triazine ring, an alkyl group, and an alkoxy group; however, when at least one of $R^3$ and $R^4$ is a halogen-substituted alkyl group, more satisfactory polymerization activity can be easily obtained, and when both represent a halogen-substituted alkyl group, the polymerization activity is particularly satisfactory.

Regarding the organic group bonded by an unsaturated bond conjugatable with a triazine ring, any known organic group may be used; however, the organic group is preferably an organic group having 2 to 30 carbon atoms, and more preferably 2 to 14 carbon atoms. Specific examples of such an organic group include an aryl group having 6 to 14 carbon atoms, such as a phenyl group, a methoxyphenyl group, a p-methylthiophenyl group, a p-chlorophenyl group, a 4-biphenylyl group, a naphthyl group, or a 4-methoxy-1-naphthyl group; and an alkenyl group having 2 to 14 carbon atoms, such as a vinyl group, a 2-phenylethenyl group, or a 2-(substituted phenyl)ethenyl group. Meanwhile, examples of the substituent carried by the substituted phenyl group include an alkyl group having 1 to 6 carbon atoms, such as a methyl group, an ethyl group, or a propyl group; an alkoxy group having 1 to 6 carbon atoms, such as a methoxy group, an ethoxy group, or a propoxy group; an akylthio group having 1 to 6 carbon atoms, such as a methylthio group, an ethylthio group, or a propylthio group; a phenyl group; and a halogen atom.

Furthermore, with regard to $R^3$ and $R^4$, the alkyl group and the alkoxy group may have a substituent, and such an alkyl group preferably has 1 to 10 carbon atoms. Examples include an unsubstituted alkyl group such as a methyl group, an ethyl group, an n-propyl group, an i-propyl group, an n-butyl group, or an n-hexyl group; and a halogen-substituted alkyl group such as a trichloromethyl group, a tribromomethyl group, or an α,α,β-trichloroethyl group. Furthermore, the alkoxy group preferably has 1 to 10 carbon atoms, and examples include an unsubstituted alkoxy group such as a methoxy group, an ethoxy group, or a butoxy group; and an alkoxy group substituted with an amino group, such as a 2-{N,N-bis(2-hydroxyethyl)amino}ethoxy group, a 2-{N-hydroxyethyl-N-ethylamino}ethoxy group, a 2-{N-hydroxyethyl-N-methylamino}ethoxy group, or a 2-{N,N-diallylamino}ethoxy group.

Specific examples of a trihalomethyl group-substituted s-triazine compound represented by General Formula (3)

described above include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis trichloromethyl)-s-triazine, and 2-[2-{N,N-diallylamino}ethoxy]-4,6-bis(trichloromethyl)-s-triazine.

Among the triazine compounds mentioned above as examples, particularly preferred is 2,4,6-tris(trichloromethyl)-s-triazine, from the viewpoint of polymerization activity.

The triazine compounds described above may be used singly or as mixtures of two or more kinds thereof.

Furthermore, in a case in which the above-described triazine compound is used as the photoacid generator (C3), it is particularly preferable to use each of an aromatic tertiary amine compound and an aliphatic tertiary amine compound as the tertiary amine compound (C2).

Regarding the aromatic tertiary amine compound and the aliphatic tertiary amine compound, any compound described above as the tertiary amine compound (C2) can be used without any limitations, and it is preferable to use the two in combination such that the mass ratio of the two (aromatic tertiary amine compound):(aliphatic tertiary amine compound) is in the range of 3:97 to 97:3, preferably 25:75 to 90:10, and more preferably 40:60 to 80:20.

The use amount of the photoacid generator (C3) is not particularly limited; however, the use amount is usually 10 parts by mass to 2,000 parts by mass, preferably 20 parts by mass to 1,000 parts by mass, and more preferably 50 parts by mass to 800 parts by mass, with respect to 100 parts by mass of the photosensitizing compound (C1). Furthermore, the use amount of the photoacid generator (C3) is preferably 0.001 parts by mass to 10 parts by mass, more preferably 0.05 parts by mass to 5 parts by mass, and even more preferably 0.1 parts by mass to 3 parts by mass, with respect to 100 parts by mass of the polymerizable monomer (A).
<Other Additives>

In the photocurable composition of the present invention, other known additives can be incorporated, in addition to the components (A) to (C) described above, to the extent that the effects are not impaired. Specific examples include a polymerization inhibitor and an ultraviolet absorber. Furthermore, since a filler having an average particle size of less than 100 nm is not likely to have a structural color, a filler having a particle size that is sufficiently smaller than such a wavelength of light and does not easily affect the color tone or transparency can be incorporated.

In the present invention, as described above, even if a coloring substance such as a pigment, is not used, the range of color tone that can be covered by one kind of paste (photocurable composition) is wide, broad color tone adaptability to natural teeth is obtained with pastes of fewer color types, and satisfactory restoration is enabled. Therefore, an embodiment in which a pigment that has a risk of being discolored with a lapse of time is not incorporated is preferred. However, according to the present invention, it is not meant to deny the incorporation of a pigment itself, and a pigment may be incorporated to the extent that will not interfere with a colored light caused by interference, scattering or the like of the spherical filler. Specifically, a pigment in an amount of about 0.0003 parts by mass to 0.04 parts by mass, and preferably about 0.001 parts by mass to 0.03 parts by mass, with respect to 100 parts by mass of the polymerizable monomer (A) may be incorporated.

The photocurable composition of the present invention is particularly suitably used as a dental filling restorative material represented by a photocurable composite resin such as described above; however, the use is not limited thereto, and the photocurable composition can also be suitably used in other use applications. Examples of such applications include dental cement and a restorative material for abutment construction.

EXAMPLES

Hereinafter, the present invention will be more specifically described by way of Examples; however, the present invention is not intended to be limited to these Examples.

The methods for measuring various physical properties according to the present invention are respectively as follows.

(1) Average Particle Size

Photographs of a powder were taken by a scanning electron microscope (manufactured by Philips N. V., "XL-30S"), and the number of whole particles (30 particles or more) observed within a unit viewing field of the photographs and the primary particle size (maximum diameter) of the whole particles were respectively measured. Based on the measured values thus obtained, the average particle size was calculated by the following formula.

$$\bar{x} = \frac{\sum_{i=1}^{n} x_i}{n} \text{(Number average)}$$

($n$: number of particle, $x_i$: primary particle size (maximum diameter) of $i$-$th$ particle)

(2) Abundance Proportion of Average Particle-Sized Particles

The number of particles having a particle size within the range of 5% greater or less than the average particle size obtained in the above section (1) was measured, and this number was divided by the number of particles (30 or more) observed within a unit viewing field of the photograph. The value thus obtained was subtracted from 1, and the resultant was multiplied by 100. Thus, the proportion of particles that are present in the range of 5% greater or less than the average particle size was calculated, and this was designated as the abundance proportion of the average particle-sized particles.

(3) Average Uniformity

A photograph of a powder was taken with a scanning electron microscope, and for the particles observed within a unit viewing field of the photograph, the number (n: 30 or more), the maximum diameter of each particle as the major axis (Li), and the diameter in a direction orthogonally intersecting the major axis as the minor axis (Bi) were determined. Thus, the average uniformity was calculated by the following formula.

$$\text{Average uniformity} = \frac{\sum_{i=1}^{n} Bi/Li}{n}$$

(4) Average Particle Size of Composite Filler 0.1 g of a composite filler was dispersed in 10 mL of ethanol, and the dispersion was irradiated with ultrasonic waves for 20 minutes. The median diameter of volume statistics was determined by applying an optical model "Fraunhofer" using a particle size distribution meter ("LS230", manufactured by Beckman Coulter, Inc.) according to a laser diffraction-scattering method.

(5) Measurement of Refractive Index

<Refractive Index of Polymerizable Monomer (A)>

The refractive index of a polymerizable monomer (or a mixture of polymerizable monomers) used was measured in a constant temperature chamber at 25° C. using an Abbe refractometer (manufactured by Atago Co., Ltd.).

<Refractive Index (nP) of Polymer of Polymerizable monomer (A)>

The refractive index of a polymer of polymerizable monomers (or a mixture of polymerizable monomers) used was measured using a polymer polymerized under conditions almost the same as the polymerization conditions in a cavity, in a constant temperature chamber at 25° C. using an Abbe refractometer (manufactured by Atago Co., Ltd.).

That is, a uniform polymerizable monomer (or a mixture of polymerizable monomers) obtained by mixing 0.2% by mass of camphorquinone, 0.3% by mass of ethyl N,N-dimethyl-p-benzoate, and 0.15% by mass of hydroquinone monomethyl ether was introduced into a mold having a through-hole having a size of 7 mmφ×0.5 mm, and a polyester film was pressure-welded on both surfaces. Subsequently, the polymerizable monomer was cured by irradiating the monomer with light through one surface for 20 seconds using a halogen type dental light irradiator ("Demetron LC", manufactured by Sybron Dental Specialties, Inc.) at a light quantity of 500 mW/cm², and then the cured product was removed from the mold. Thus, a polymer obtained by polymerizing the polymerizable monomer was produced. When the polymer was placed in an Abbe refractometer (manufactured by Atago Co., Ltd.), for the purpose of tightly adhering the polymer with the measuring surface, the sample was not dissolved, but a solvent having a refractive index higher than that of the sample (bromonaphthalene) was dropped onto the sample, and the refractive index was measured.

<Refractive Indices of Spherical Inorganic Filler and Irregularly Shaped Inorganic Filler>

The refractive indices of a spherical inorganic filler and an irregularly shaped inorganic filler used were measured according to a liquid immersion method using an Abbe refractometer (manufactured by Atago Co., Ltd.).

That is, in a constant temperature chamber at 25° C., in a 100-mL sample bottle, 1 g of a spherical inorganic filler, an irregularly shaped inorganic filler, or a surface-treated product thereof was dispersed in 50 mL of anhydrous toluene. While this dispersion liquid was stirred with a stirrer, 1-bromotoluene was added dropwise in small amounts, the refractive index of the dispersion liquid at the time point when the dispersion liquid became most transparent was measured, and the value thus obtained was designated as the refractive index of the inorganic filler.

(6) Evaluation of Colored Light by Visual Inspection

A paste of each of the photocurable compositions produced in Examples and Comparative Examples was introduced into a mold having a through-hole having a size of 7 mmφ×1 mm, and a polyester film was pressure-welded on both surfaces. The paste was cured by irradiating the paste with light through both surfaces for 20 seconds with a visible light irradiator (manufactured by Tokuyama Corp., POWER LIGHT), and then the resultant was removed from the mold. The cured product was mounted on an adhesive surface of a black tape (carbon tape) that measured about 10 mm on each edge, and the color tone of the colored light was checked by visual inspection.

(7) Wavelength of Colored Light

A paste of each of the photocurable compositions produced in Examples and Comparative Examples was introduced into a mold having a through-hole having a size of 7 mmφ×1 mm, and a polyester film was pressure-welded on both surfaces. The paste was cured by irradiating the paste with light through both surfaces for 20 seconds with a visible light irradiator (manufactured by Tokuyama Corp., POWER LIGHT), and then the resultant was removed from the mold. The spectral reflectance was measured using a color difference meter (manufactured by Tokyo Denshoku Co., Ltd., "TC-1800 MKII") on a black background (backing having a value of 1 according to the Munsell Color System) and on a white background (backing having a value of 9.5 according to the Munsell Color System), and the maximum point of the reflectance on the black background was designated as the wavelength of the colored light.

(8) Hue, Value, and Chroma

A paste of each of the photocurable compositions produced in Examples and Comparative Examples was introduced into a mold having a through-hole having a size of 7 mmφ×1 mm, and a polyester film was pressure-welded on both surfaces. The paste was cured by irradiating the paste with light through both surfaces for 20 seconds with a visible light irradiator (manufactured by Tokuyama Corp., POWER LIGHT), and then the resultant was removed from the mold. The hue (H), value (V), and chroma (C) based on the Munsell Color System were measured according to JIS Z8722 for each of the cured products on a black background (backing having a value of 1 according to the Munsell Color System) and on a white background (backing having a value of 9.5 according to the Munsell Color System), using a color difference meter (manufactured by Tokyo Denshoku Co., Ltd., "TC-1800 MKII").

(9) Evaluation of Color Tone Adaptability

A hard resin tooth that reproduced an incisal part loss cavity (width 2 mm, depth 1 mm) of the upper right No. 1, a hard resin tooth that reproduced a Class I cavity (diameter 4 mm, depth 2 mm) of the lower right No. 6, or a hard resin tooth that reproduced a tooth cervix loss cavity (diameter 4 mm, depth 2 mm) of upper right No. 3 was used. The cavity was filled with a paste of each of the photocurable compositions, subsequently the paste was cured by irradiating the paste with light for 20 seconds using a visible light irradiator (manufactured by Tokuyama Corp., POWER LIGHT), subsequently the paste was polished, and the color tone adaptability was checked by visual inspection. The evaluation criteria are shown below. Furthermore, for the hard resin teeth, a hard resin tooth of high chroma (corresponding to A4) and a hard resin tooth of low chroma (corresponding to A1) in the class of A system (red-brown) according to Shade Guide "VITAPAN Classical (registered trademark)", and a hard resin tooth of high chroma (corresponding to B4) and a hard resin tooth of low chroma (corresponding to B1) in the class of B system (red-yellow) according to Shade Guide "VITAPAN Classical (registered trademark)" were used.

Evaluation Criteria

5: The color tone of the restoration product is indistinguishable from that of the hard resin tooth.
4: The color tone of the restoration product highly matches with that of the hard resin tooth.
3: The color tone of the restoration product is similar to that of the hard resin tooth.
2: The color tone of the restoration product is similar to that of the hard resin tooth; however, adaptability is not satisfactory.
1: The color tone of the restoration product does not match with that of the hard resin tooth.

(10) Change in Color Tone Over Time

A paste of each of the photocurable compositions produced in Examples and Comparative Examples was introduced into a mold having a through-hole having a size of 7 mm×1 mm, and a polyester film was pressure-welded on both surfaces. The paste was cured by irradiating the paste with light through both surfaces for 20 seconds with a visible light irradiator (manufactured by Tokuyama Corp., POWER LIGHT), and then the resultant was removed from the mold. The cured product was stored in water at 37° C. for 4 months, and the color tone was measured using a color difference meter (manufactured by Tokyo Denshoku Co., Ltd., "TC-1800 MKII"). The difference between the color tones before and after the storage is represented by ΔE* in the CIELab, according to the following formula.

$$\Delta E^* = \{(\Delta L^*)^2 + (\Delta a^*)^2 + (\Delta b)^2\}^{1/2}$$

$$\Delta L^* = L1^* - L2^*$$

$$\Delta a^* = a1^* - a2^*$$

$$\Delta b^* = b1^* - b2^*$$

in which, $L1^*$: psychometric lightness index of cured product after storage, $a1^*$ and $b1^*$: psychometric chroma coordinates of cured product after storage, $L2^*$: psychometric lightness index of cured product before storage, $a2^*$ and $b2^*$: psychometric chroma coordinates of cured product before storage, $\Delta E^*$: amount of change in color tone.

(11) Hardness (Vickers Hardness) of Cured Product

A paste of each of the photocurable compositions produced in Examples and Comparative Examples was introduced into a mold made of polytetrafluoroethylene and having a through-hole having a size of 6 mmφ×1.0 mm, and a polypropylene film was pressure-welded on both surfaces. The paste was irradiated for 20 seconds using a visible light irradiator (manufactured by Tokuyama Corp., POWER LIGHT) such that the light intensity at the irradiation surface would be 640 mW/cm² to 650 mW/cm², through one surface adherently to the polypropylene film, and thus a cured product was produced. The Vickers hardness of the light-irradiated surface of the cured product thus obtained was determined using a Vickers indenter in a microhardness meter (manufactured by Matsuzawa Co., Ltd., "MHT-1 type"), by means of the diagonal length of an indentation produced in the specimen under a load of 100 gf for a load retention time of 30 seconds.

(12) Bending Strength

A paste of the photocurable compositions produced in Examples and Comparative Examples was charged into a rectangular prism-shaped mold made of stainless steel and having a size of 2 mm×2 mm×25 mm, and the paste was irradiated with light using a visible light irradiator (manufactured by Tokuyama Corp., POWER LIGHT) adherently to the polypropylene, in a state in which a polypropylene film was pressure-welded to the mold, by changing the place from one surface three times for 20 seconds each time so that lights would hit the entirety, so that the light intensity at the irradiated surface would be 640 mW/cm² to 650 mW/cm². Next, light irradiation of three times for 20 seconds each time was carried out through the opposite surface similarly adherently to the polypropylene, and a cured product was obtained. The cured product was trimmed into a rectangular prism shape having a size of 2 mm×2 mm×25 mm with a #800 water-resistant polishing paper, this sample was mounted on a testing machine (manufactured by Shimadzu Corp., "AUTOGRAPH AG5000D"), and the three-point bending fracture strength was measured at a distance between two fulcrums of 20 mm and a cross-head speed of 1 mm/min.

(13) Stability to Ambient Light Test

The distance between a light source and a sample was set such that the surface of a paste of each of the photocurable compositions produced in Example and Comparative Examples would be 10,000 lux. A dental light (light source: halogen light, manufactured by Takara Belmont Corp.) was used as a light source, and the distance between the sample and the light source was set such that the illuminance measured with an illuminometer (Tokyo Garasu Kikai Co., Ltd., "DIGITAL LUX METER: FL-1330") would become the illuminance value described above. The light intensity at this irradiated surface was 0.3 mW/cm². 0.03 g of a sample of the photocurable composition thus produced was weighed and collected on a polypropylene film, and the sample was irradiated with the dental light for a predetermined time. Subsequently, the sample was pressed, and the time at which the interior of the sample began to solidify was measured. Meanwhile, the irradiation time was set to an interval of 5 seconds. As this time is longer, superior stability to ambient light is obtained, and therefore, a satisfactory operation margin time can be obtained. Meanwhile, the illuminometer used had a sensitivity of 400 nm to 700 nm.

The compounds used in Examples and Comparative Examples are as follows.

[Polymerizable Monomers]
1,6-Bis(methacrylethyloxycarbonylamino)trimethylhexane (hereinafter, abbreviated to "UDMA")
Triethylene glycol dimethacrylate (hereinafter, abbreviated to "3G")
2,2-Bis[(3-methacryloyloxy-2-hydroxypropyloxy)phenyl]propane (hereinafter, abbreviated to "bis-GMA")

[Polymerization Initiators]
Camphorquinone (hereinafter, abbreviated to "CQ")
Ethyl p-N,N-dimethylaminobenzoate (hereinafter, abbreviated to "DMBE")
N-methyldiethanolamine (hereinafter, abbreviated to "MDEOA")

Diphenyliodonium 2-carboxylate monohydrate (hereinafter, abbreviated to "DPICH")
Diphenyliodonium nitrate (hereinafter, abbreviated to "DPIN")
Diphenyliodonium chloride (hereinafter, abbreviated to "DPIC")
2,4,6-Tris(trichloromethyl)-s-triazine (hereinafter, abbreviated to "TCT")
2-Phenyl-4,6-bis(trichloromethyl)-s-triazine (hereinafter, abbreviated to "PBCT")
2-(p-Chlorophenyl)-4,6-bis(trichloromethyl)-s-triazine (hereinafter, abbreviated to "CBCT")
[Polymerization Inhibitor]
Hydroquinone monomethyl ether (hereinafter, abbreviated to "HQME")
[Colorant]
Titanium dioxide (white pigment)
Pigment Yellow (yellow pigment)
Pigment Red (red pigment)
Pigment Blue (blue pigment)
[Preparation of Mixture of Polymerizable Monomers]

The polymerizable monomers shown in Table 1 were mixed, and polymerizable monomers M1, M2, and M3 were prepared. The values in the parentheses in Table 1 represent the use amounts (unit: parts by mass) of the respective polymerizable monomers.

TABLE 1

| | | Refractive index | |
|---|---|---|---|
| | Polymerizable monomer | Before curing | After curing |
| M1 | UDMA(60)/3G(40) | 1.474 | 1.509 |
| M2 | bis-GMA(50)/3G(50) | 1.506 | 1.540 |
| M3 | bis-GMA(30)/3G(70) | 1.488 | 1.528 |

[Production of Spherical Inorganic Filler and Irregularly Shaped Inorganic Filler]

A spherical inorganic filler was produced by the method described in Japanese Unexamined Patent Application, Publication. No. S58-110414, Japanese Unexamined Patent Application, Publication No. S58-156524, and the like. That is, a spherical inorganic filler was produced using a so-called sol-gel method of adding a mixed solution including a hydrolyzable organosilicon compound (tetraethyl silicate or the like) and a hydrolyzable organic titanium group metal compound (tetrabutyl zirconate, tetrabutyl titanate, or the like) into an ammoniacal alcohol (for example, methanol, ethanol, isopropyl alcohol, or isobutyl alcohol) solution having aqueous ammonia incorporated therein, performing hydrolysis, and precipitating out a reaction product.

An irregularly shaped inorganic filler was produced by the method described in Japanese Unexamined Patent Application, Publication. No. H02-132102, Japanese Unexamined Patent Application, Publication No. H03-197311, or the like. That is, an irregularly shaped inorganic filler was produced using a method of dissolving an alkoxysilane compound in an organic solvent, adding water to this solution to perform partial hydrolysis, subsequently adding thereto an alkoxide of another metal and an alkali metal compound to be compositized, thereby performing hydrolysis to produce a gel-like material, drying the gel-like material, subsequently pulverizing the dried product as necessary, and calcining the pulverization product.

The spherical inorganic fillers and irregularly shaped inorganic fillers used in Examples are shown in Table 2.

TABLE 2

| | Composition and shape of inorganic filler | | Average particle size nm | Refractive index | Abundance proportion of average particle-sized particles[1] % | Average uniformity |
|---|---|---|---|---|---|---|
| | Composition (mol %) | Shape | | | | |
| PF1 | $SiO_2/ZrO_2/Na_2O$ = 89.8/9.0/1.2 | Spherical | 178 | 1.515 | 91 | 0.98 |
| PF2 | $SiO_2/ZrO_2/Na_2O$ = 89.8/9.0/1.2 | Spherical | 230 | 1.515 | 92 | 0.97 |
| PF3 | $SiO_2/ZrO_2/Na_2O$ = 89.8/9.0/1.2 | Spherical | 281 | 1.515 | 94 | 0.96 |
| PF4 | $SiO_2/ZrO_2/Na_2O$ = 89.8/9.0/1.2 | Spherical | 80 | 1.515 | 92 | 0.94 |
| PF5 | $SiO_2/ZrO_2/Na_2O$ = 89.8/9.0/1.2 | Spherical | 280 | 1.515 | 87 | 0.92 |
| PF6 | $SiO_2/ZrO_2/Na_2O$ = 88.7/10.8/1.2 | Spherical | 282 | 1.522 | 93 | 0.92 |
| PF7 | $SiO_2/ZrO_2/Na_2O$ = 83.9/14.3/1.8 | Spherical | 286 | 1.542 | 91 | 0.90 |
| PF8 | $SiO_2/TiO_2/Na_2O$ = 90.1/9.4/1.2 | Spherical | 280 | 1.522 | 95 | 0.95 |
| PF9 | $SiO_2/ZrO_2/Na_2O$ = 88.7/10.8/1.2 | Spherical | 340 | 1.522 | 91 | 0.93 |
| PF10 | $SiO_2/ZrO_2/Na_2O$ = 88.7/10.8/1.2 | Spherical | 260 | 1.522 | 93 | 0.94 |
| PF11 | $SiO_2/ZrO_2/Na_2O$ = 89.8/9.0/1.2 | Irregularly shaped | 500 | 1.515 | 50 | — |

[1]The abundance proportion of average particle-sized particles is the proportion (%) of particles existing in the range of 5% greater or less than the average particle size.

[Production of Composite Filler]

0.5% by mass of a thermal polymerization initiator (azobisisobutyronitrile) was dissolved in advance in the polymerizable monomer shown in Table 1, a spherical inorganic filler was added in a predetermined amount (Table 3) and mixed with the solution, and the mixture was produced into a paste using a mortar. This was polymerized and cured by heating for one hour under nitrogen pressurization at 95° C. This cured product was pulverized using a vibratory ball mill, and a surface treatment was carried out by heating the cured product to reflux for 5 hours at 0° C. in ethanol using 0.02% by mass of γ-methacryloyloxypropyltrimethoxysilane. Thus, composite fillers CF1 and CF2 shown in the following Table 3 were obtained. The values in the parentheses in Table 3 represent the use amounts (unit: parts by mass) of the polymerizable monomer and the spherical inorganic filler.

TABLE 3

| | Polymerizable monomer | Spherical inorganic filler | Filler filling ratio (wt %) | Average particle size (μm) |
|---|---|---|---|---|
| CF1 | M1(100) | PF3(300) | 75 | 30 |
| CF2 | M2(100) | PF3(300) | 75 | 28 |

Examples 1 to 12

The polymerization initiators shown in Table 4 and 0.15 parts by mass of HQME were added to and mixed into polymerizable monomer M1 or M2, and thus a uniform polymerizable monomer composition was prepared. Next, each of the fillers shown in Table 4 was weighed in a mortar, the polymerizable monomer composition was slowly added thereto under red light, and the mixture was sufficiently kneaded in the dark. Thus, a uniform paste was obtained. Furthermore, this paste was degassed under reduced pressure to eliminate air bubbles, and thus a photocurable composition was prepared. For the photocurable composition (filling restorative material) thus obtained, various physical properties were evaluated based on the above-described methods. The compositions of the photocurable compositions are shown in Table 4, and the evaluation results are shown in Table 6 and Table 7. The values in the parentheses in Table 1 represent the use amounts (unit: parts by mass) of the polymerizable monomer, the filler, and the polymerization initiators.

Comparative Examples 1 to 8

The polymerization initiators shown in Table 5 and 0.15 parts by mass of HQME were added to and mixed into polymerizable monomer M1, M2, or M3, and thus a uniform polymerizable monomer composition was prepared. Next, each of the fillers shown in Table 5 was weighed in a mortar, the polymerizable monomer composition was slowly added thereto under red light, and the mixture was sufficiently kneaded in the dark. Thus, a uniform paste was obtained. Furthermore, this paste was degassed under reduced pressure to eliminate air bubbles, and thus a photocurable composition was prepared. For the photocurable composition (filling restorative material) thus obtained, various physical properties were evaluated based on the above-described methods. The compositions of the photocurable compositions are shown in Table 5, and the evaluation results are shown in Table 6 and Table 7. The values in the parentheses in Table 5 represent the use amounts (unit: parts by mass) of the polymerizable monomer, the filler, and the polymerization initiators, and the symbol "-" represents that the component is not used.

Comparative Example 9

The polymerization initiators shown in Table 5 and 0.15 parts by mass of HQME were added to and mixed into polymerizable monomer M1, and thus a uniform polymerizable monomer composition was prepared. Next, the filler shown in Table 5 was weighed in a mortar, the polymerizable monomer composition was slowly added thereto under red light. Furthermore, 0.001 parts by mass of titanium dioxide (white pigment), 0.001 parts by mass of Pigment Yellow (yellow pigment), 0.0005 parts by mass of Pigment Red (red pigment), and 0.0002 parts by mass of Pigment Blue (blue pigment) were added to the composition, and the mixture was sufficiently kneaded in the dark. Thus, a uniform paste was obtained. Furthermore, this paste was degassed under reduced pressure to eliminate air bubbles, and thus a photocurable composition was prepared. Through an evaluation by visual inspection, a color tone (corresponding to A4) that matched with A system of high chroma hard resin teeth was obtained. Subsequently, various physical properties were evaluated based on the above-described method. The compositions of the photocurable compositions are shown in Table 5, and the evaluation results are shown in Table 6 and Table 7.

TABLE 4

| | | | | | Polymerization initiator | | |
|---|---|---|---|---|---|---|---|
| | Polymerizable monomer | Filler | Method of adding filler | Refractive index difference[1] | Photosensitizing compound | Tertiary amine | Photo-acid generator |
| Example 1 | M1 (100) | PF2 (150) | Added as spherical filler | 0.006 | CQ (0.3) | DMBE (0.3) | DPIN (0.3) |
| Example 2 | M1 (100) | PF3 (150) | Added as spherical filler | 0.006 | CQ (0.3) | DMBE (0.3) | DPICH (0.3) |
| Example 3 | M1 (100) | PF3 (300) | Added as composite filler CF1 (400) | 0.006 | CQ (0.3) | DMBE (0.3) | DPICH (0.3) |

TABLE 4-continued

| | Polymerizable monomer | Filler | Method of adding filler | Refractive index difference[1] | Polymerization initiator | | |
|---|---|---|---|---|---|---|---|
| | | | | | Photosensitizing compound | Tertiary amine | Photo-acid generator |
| Example 4 | M1 (100) | PF3 (210) | Added as spherical filler PF3 (90) and composite filler CF1 (160) | 0.006 | CQ (0.3) | DMBE (0.3) | DPICH (0.3) |
| Example 5 | M1 (100) | PF3 (150) | Added as spherical filler | 0.006 | CQ (0.3) | DMBE (0.3) | TCT (0.3) |
| Example 6 | M1 (100) | PF3 (150) | Added as spherical filler | 0.006 | CQ (0.3) | DMBE (0.2)/ MDEOA (0.2) | TCT (0.3) |
| Example 7 | M1 (100) | PF6 (150) | Added as spherical filler | 0.013 | CQ (0.3) | DMBE (0.2)/ MDEOA (0.2) | PBCT (0.3) |
| Example 8 | M2 (100) | PF7 (150) | Added as spherical filler | 0.002 | CQ (0.3) | DMBE (0.2)/ MDEOA (0.2) | CBCT (0.3) |
| Example 9 | M1 (100) | PF8 (150) | Added as spherical filler | 0.013 | CQ (0.3) | DMBE (0.3) | DPIC (0.3) |
| Example 10 | M1 (100) | PF9 (150) | Added as spherical filler | 0.006 | CQ (0.3) | DMBE (0.3) | DPICH (0.3) |
| Example 11 | M1 (100) | PF7 (150) | Added as spherical filler | 0.033 | CQ (0.3) | DMBE (0.3) | DPICH (0.3) |
| Example 12 | M1 (100) | PF10 (150) | Added as spherical filler | 0.013 | CQ (0.3) | DMBE (0.3) | DPICH (0.3) |

[1] Refractive index of filler-refractive index of polymer of polymerizable monomer

TABLE 5

| | Polymerizable monomer | Filler | Method of adding filler | Refractive index difference[1] | Polymerization initiator | | |
|---|---|---|---|---|---|---|---|
| | | | | | Photosensitizing compound | Tertiary amine | Photo-acid generator |
| Comparative Example 1 | M1 (100) | PF4 (150) | Added as spherical filler | 0.006 | CQ (0.3) | DMBE (0.3) | DPICH (0.3) |
| Comparative Example 2 | M1 (100) | PF5 (150) | Added as spherical filler | 0.006 | CQ (0.3) | DMBE (1.0) | — |
| Comparative Example 3 | M1 (100) | PF11 (150) | Added as irregularly shaped filler | 0.006 | CQ (0.3) | DMBE (0.3) | DPICH (0.3) |
| Comparative Example 4 | M2 (100) | PF3 (150) | Added as spherical filler | −0.025 | CQ (0.3) | DMBE (0.3) | DPICH (0.3) |
| Comparative Example 5 | M2 (100) | PF3 (300) | Added as composite filler CF2 (400) | −0.025 | CQ (0.3) | DMBE (0.3) | DPICH (0.3) |
| Comparative Example 6 | M3 (100) | PF3 (150) | Added as spherical filler | −0.013 | CQ (0.3) | DMBE (0.3) | DPICH (0.3) |
| Comparative Example 7 | M1 (100) | PF1 (150) | Added as spherical filler | 0.006 | CQ (0.3) | DMBE (0.3) | DPICH (0.3) |
| Comparative Example 8 | M1 (100) | PF5 (150) | Added as spherical filler | 0.006 | CQ (0.6) | DMBE (2.0) | — |
| Comparative Example 9 | M1 (100) | PF1 (150) | Added as spherical filler | 0.006 | CQ (0.3) | DMBE (0.3) | DPICH (0.3) |

[1] Refractive index of filler-refractive index of polymer of polymerizable monomer

TABLE 6

| | Visual evaluation of colored light | Wavelength (nm) of colored light on black background | Wavelength (nm) of colored light on white background | Color tone on black background | | | Color tone on white background | | | Change over time in color tone ΔE* |
|---|---|---|---|---|---|---|---|---|---|---|
| | | | | Hue (H) | Value (V) | Chroma (C) | Hue (H) | Value (V) | Chroma (C) | |
| Example 1 | Yellow | 603 | No maximum | 5.32Y | 3.10 | 0.50 | 2.15Y | 7.52 | 1.05 | 2.0 |
| Example 2 | Red | 750 | No maximum | 9.97YR | 3.16 | 0.07 | 1.79Y | 7.31 | 0.86 | 1.3 |
| Example 3 | Red | 750 | No maximum | 9.87YR | 3.08 | 0.10 | 1.80Y | 7.11 | 0.82 | 1.4 |
| Example 4 | Red | 750 | No maximum | 9.91YR | 3.12 | 0.08 | 1.80Y | 7.22 | 0.85 | 1.2 |
| Example 5 | Red | 750 | No maximum | 0.23Y | 3.22 | 0.22 | 1.82Y | 7.34 | 0.98 | 1.3 |
| Example 6 | Red | 750 | No maximum | 0.21Y | 3.18 | 0.19 | 1.80Y | 7.32 | 0.94 | 1.3 |
| Example 7 | Red | 758 | No maximum | 6.41YR | 3.54 | 0.21 | 1.30Y | 7.26 | 0.97 | 1.4 |
| Example 8 | Red | 746 | No maximum | 9.76YR | 3.32 | 0.24 | 1.83Y | 7.46 | 1.13 | 1.6 |
| Example 9 | Red | 754 | No maximum | 0.87YR | 3.21 | 0.09 | 1.56Y | 7.15 | 0.83 | 1.8 |
| Example 10 | Red | 736 | No maximum | 3.21RP | 3.84 | 0.25 | 1.66Y | 7.35 | 0.32 | 1.7 |
| Example 11 | Red | 741 | No maximum | 9.26YR | 3.45 | 0.24 | 1.86Y | 7.56 | 1.08 | 1.5 |
| Example 12 | Red | 670 | No maximum | 1.11Y | 3.32 | 0.33 | 1.86Y | 7.66 | 1.10 | 1.4 |
| Comparative Example 1 | None | 405 | No maximum | 5.44PB | 1.40 | 2.19 | 4.78Y | 8.16 | 2.10 | 1.6 |
| Comparative Example 2 | Pale red | 741 | No maximum | 8.23YR | 5.10 | 0.04 | 2.51Y | 7.88 | 0.86 | 2.0 |
| Comparative Example 3 | None | No maximum | No maximum | 6.74B | 5.73 | 0.79 | 1.94Y | 5.89 | 2.53 | 2.1 |
| Comparative Example 4 | Blue | 492 | No maximum | 5.78B | 4.58 | 0.72 | 2.10Y | 6.12 | 2.36 | 1.6 |
| Comparative Example 5 | Blue | 492 | No maximum | 5.64B | 4.44 | 0.64 | 2.05Y | 6.05 | 2.21 | 1.7 |
| Comparative Example 6 | Blue | 488 | No maximum | 5.56B | 4.61 | 0.68 | 2.01Y | 6.07 | 2.31 | 1.6 |
| Comparative Example 7 | Blue | 485 | No maximum | 6.52B | 2.53 | 4.01 | 4.17Y | 8.06 | 1.20 | 1.5 |
| Comparative Example 8 | Pale red | 741 | No maximum | 8.97YR | 5.32 | 0.31 | 2.88Y | 8.01 | 1.02 | 2.0 |
| Comparative Example 9 | Red | No maximum | No maximum | 5.38B | 4.13 | 0.69 | 1.94Y | 6.28 | 2.21 | 4.8 |

TABLE 7

| | Hard resin tooth | Filling site | Color tone adaptability | | | | Vickers hardness | Bending strength [MPa] | Stability to ambient light [sec] |
|---|---|---|---|---|---|---|---|---|---|
| | | | A system | | B system | | | | |
| | | | (Low chroma) | (High chroma) | (Low chroma) | (High chroma) | | | |
| Example 1 | Lower right No. 6 | Central part of occlusal surface | 3 | 3 | 4 | 4 | 35 | 151 | 100 |
| Example 2 | Lower right No. 6 | Central part of occlusal surface | 5 | 5 | 5 | 5 | 42 | 165 | 100 |
| | Upper right No. 3 | Tooth cervix | 5 | 5 | 5 | 5 | | | |
| | Upper right No. 1 | Incissal part | 5 | 5 | 5 | 5 | | | |
| Example 3 | Lower right No. 6 | Central part of occlusal surface | 5 | 5 | 5 | 5 | 40 | 158 | 100 |
| Example 4 | Lower right No. 6 | Central part of occlusal surface | 5 | 5 | 5 | 5 | 44 | 168 | 100 |
| Example 5 | Lower right No. 6 | Central part of occlusal surface | 5 | 5 | 5 | 5 | 33 | 148 | 110 |
| Example 6 | Lower right No. 6 | Central part of occlusal surface | 5 | 5 | 5 | 5 | 40 | 161 | 100 |
| Example 7 | Lower right No. 6 | Central part of occlusal surface | 5 | 5 | 5 | 5 | 38 | 158 | 100 |
| Example 8 | Lower right No. 6 | Central part of occlusal surface | 5 | 5 | 5 | 5 | 37 | 155 | 100 |
| Example 9 | Lower right No. 6 | Central part of occlusal surface | 5 | 5 | 5 | 5 | 31 | 144 | 110 |
| Example 10 | Lower right No. 6 | Central part of occlusal surface | 4 | 4 | 3 | 3 | 40 | 159 | 100 |
| Example 11 | Lower right No. 6 | Central part of occlusal surface | 4 | 5 | 4 | 5 | 39 | 160 | 100 |
| Example 12 | Lower right No. 6 | Central part of occlusal surface | 4 | 4 | 5 | 5 | 38 | 158 | 100 |

TABLE 7-continued

|  | Hard resin tooth | Filling site | Color tone adaptability | | | | Vickers hardness | Bending strength [MPa] | Stability to ambient light [sec] |
|  |  |  | A system | | B system | | | | |
|  |  |  | (Low chroma) | (High chroma) | (Low chroma) | (High chroma) | | | |
| --- | --- | --- | --- | --- | --- | --- | --- | --- | --- |
| Comparative Example 1 | Lower right No. 6 | Central part of occlusal surface | 1 | 1 | 1 | 1 | 41 | 163 | 100 |
| Comparative Example 2 | Lower right No. 6 | Central part of occlusal surface | 2 | 2 | 2 | 2 | 24 | 120 | 100 |
| Comparative Example 3 | Lower right No. 6 | Central part of occlusal surface | 1 | 1 | 1 | 1 | 33 | 146 | 100 |
| Comparative Example 4 | Lower right No. 6 | Central part of occlusal surface | 1 | 1 | 1 | 1 | 38 | 159 | 100 |
| Comparative Example 5 | Lower right No. 6 | Central part of occlusal surface | 1 | 1 | 1 | 1 | 35 | 152 | 100 |
| Comparative Example 6 | Lower right No. 6 | Central part of occlusal surface | 1 | 1 | 2 | 2 | 33 | 145 | 110 |
| Comparative Example 7 | Lower right No. 6 | Central part of occlusal surface | 1 | 1 | 2 | 2 | 39 | 158 | 100 |
| Comparative Example 8 | Lower right No. 6 | Central part of occlusal surface | 2 | 2 | 2 | 2 | 32 | 135 | 50 |
| Comparative Example 9 | Lower right No. 6 | Central part of occlusal surface | 2 | 3 | 1 | 1 | 40 | 159 | 100 |

As is understood from the results of Examples 1 to 12, it can be seen that when the polymerizable monomer and the filler satisfy the conditions defined in the present invention, the photocurable composition exhibits a colored light on a black background, satisfactory color tone adaptability is obtained, and the change over time in the color tone of a cured product thus obtainable is small. Furthermore, it can be seen that when the polymerization initiator satisfies the conditions defined in the present invention, the Vickers hardness and the bending strength are high, while the stability to ambient light is high.

As is understood from the results of Comparative Examples 1 to 7, it can be seen that when the conditions defined in the present invention are not satisfied, the photocurable compositions do not exhibit a colored light on a black background (Comparative Example 1: average particle size of the spherical inorganic filler is 80 nm, Comparative Example 3: the shape of the filler is irregular), exhibit a weak colored light (Comparative Example 2: the proportion of particles present in the range of the average particle size of the spherical filler ±5% is 87%, a photoacid generator is not included in the polymerization initiator), the colored light is bluish (Comparative Example 4 to 6: refractive index of a polymer obtained by polymerizing the polymerizable monomer refractive index of the spherical filler, Comparative Example 7: average particle size of the spherical filler <230 nm). It is understood that all of them have inferior adaptability to the color tone of the dentinal surface.

As is understood from the results of Comparative Example 9, the photocurable composition having the color tone adjusted to a color tone that matched with A system of high chroma hard resin teeth by adding a pigment to the composition shown in Comparative Example 7, exhibited red color in both on a black background and on a white background in an evaluation by visual inspection. However, the spectral reflectance was measured on a black background and a white background using a color difference meter (manufactured by Tokyo Denshoku Co., Ltd., "TC-1800 MKII"), and since the respective spectral reflection characteristics of the pigments added were observed to be overlapping with one another, the maximum of the reflectance originating from the structural color was not observed on a white background as well as on a black background. The color tone adaptability to A system of high chroma hard resin teeth (corresponding to A4) was satisfactory; however, the color tone adaptability to other model teeth was low. Furthermore, the change over time in the color tone was large.

As is understood from the results of Comparative Example 2, in a case in which a photoacid generator is not included in the polymerization initiator, the Vickers hardness and the bending strength are poor.

As is understood from the results of Comparative Example 8 in which the amount of CQ as a photosensitizing compound and the amount of DMBE as a tertiary amine compound were increased compared to Comparative Example 2, when the amounts of the photosensitizing compound and the tertiary amine compound are increased, the Vickers hardness and the bending strength were enhanced compared to Comparative Example 2; however, the stability to ambient light was decreased. As such, it is difficult to obtain a photocurable composition that achieves both the mechanical strength and the stability to ambient light, by increasing the amounts of the photosensitizing compound and the tertiary amine compound.

The invention claimed is:

1. A photocurable composition comprising: a polymerizable monomer (A); a spherical filler (B) having an average particle size in a range of 230 nm to 1,000 nm; and a polymerization initiator (C), wherein when measurement is made for the photocurable composition in a state of having formed a cured product having a thickness of 1 mm, using a color difference meter, the cured product of the photocurable composition gives out a colored light having a hue (H) of 0RP or greater and less than 10RP, 0R or greater and less than 10R, 0YR or greater and less than 10YR, or 0Y or greater and less than 10Y in the colorimetric values according to the Munsell Color System on a black background, wherein the spherical filler (B) is incorporated in a state in which a part or the entirety of the spherical filler (B) constitutes a composite filler with an organic resin matrix, into the composition, wherein 90% or more of individual particles constituting the spherical filler (B) are present in a range of 5% greater or less than the average particle size, the polymerizable monomer (A) and the spherical filler (B) satisfy requirement (X1) represented by the following Formulas (1) and (2):

$$nP < nF \qquad (1)$$

$$nF - nP \geq 0.002 \qquad (2);$$

wherein nP represents a refractive index at 25° C. of a polymer obtainable by polymerizing the polymerizable monomer (A); and nF represents a refractive index at 25° C. of the spherical filler (B), the organic resin matrix and the spherical filler (B) satisfy requirement (X2) represented by the following Formula (3):

$$nD < nF \qquad (3);$$

wherein nD represents a refractive index at 25° C. of the organic resin matrix, and the polymerization initiator (C) includes a photosensitizing compound (C1), a tertiary amine compound (C2), and a photoacid generator (C3).

2. The photocurable composition according to claim 1, wherein the photocurable composition includes an aryliodonium salt or an s-triazine compound having a trihalomethyl group as a substituent, as the photoacid generator (C3).

3. The photocurable composition according to claim 2, wherein the aryliodonium salt is an aryliodonium salt capable of producing, by a cleavage reaction, an acid having an acid dissociation constant of −3.0 or higher in water at 25° C.

4. The photocurable composition according to claim 2, wherein the photocurable composition includes an s-triazine compound having a trihalomethyl group as a substituent as the photoacid generator (C3), and includes an aromatic tertiary amine compound and an aliphatic tertiary amine compound as the tertiary amine compound (C2).

5. The photocurable composition according to claim 1, wherein the photocurable composition includes a plurality of (meth)acrylic compounds as the polymerizable monomer (A), and the refractive index at 25° C. of the polymerizable monomer (A) is in a range of 1.38 to 1.55.

6. The photocurable composition according to claim 1, wherein the spherical filler (B) is spherical silica-titanium group oxide-based composite oxide particles, and the refractive index thereof at 25° C. is in a range of 1.45 to 1.58.

7. A dental filling restorative material consisting of the photocurable composition according to claim 1.

8. The dental filling restorative material according to claim 7, wherein the average particle size of the spherical filler (B) is in a range of 230 nm to 500 nm, and the dental filling restorative material is to be used for the restoration of a cavity having a dentine positioned at a surface of a deep part.

* * * * *